(12) United States Patent
Vasta et al.

(10) Patent No.: US 10,905,702 B2
(45) Date of Patent: Feb. 2, 2021

(54) INHIBITION OF GALECTIN 3 BINDING TO THE AIRWAY EPITHELIAL SURFACE TO TREAT OR PREVENT SEPTIC SHOCK RESULTING FROM INFLUENZA AND SUBSEQUENT PNEUMOCOCCAL PNEUMONIA INFECTION

(71) Applicants: Gerardo Vasta, Columbia, MD (US); Lai-Xi Wang, Ellicott City, MD (US)

(72) Inventors: Gerardo Vasta, Columbia, MD (US); Lai-Xi Wang, Ellicott City, MD (US)

(73) Assignees: UNIVERSITY OF MARYLAND, BALTIMORE, Baltimore, MD (US); UNIVERSITY OF MARYLAND, College Park, MD (US)

( * ) Notice: Subject to any disclaimer, the term of this patent is extended or adjusted under 35 U.S.C. 154(b) by 0 days.

(21) Appl. No.: 16/258,228

(22) Filed: Jan. 25, 2019

(65) Prior Publication Data
US 2019/0142853 A1    May 16, 2019

Related U.S. Application Data

(63) Continuation-in-part of application No. PCT/US2017/043739, filed on Jul. 25, 2017.
(Continued)

(51) Int. Cl.
*A61K 31/7004*   (2006.01)
*A61K 31/7056*   (2006.01)
*A61K 31/724*    (2006.01)
*A61P 31/00*     (2006.01)
*A61P 11/00*     (2006.01)
*A61K 9/107*     (2006.01)
*A61K 31/351*    (2006.01)
*A61K 31/4192*   (2006.01)
*A61K 31/7016*   (2006.01)
*A61K 31/43*     (2006.01)
*A61K 31/7036*   (2006.01)
*A61K 31/7048*   (2006.01)
*A61K 45/06*     (2006.01)

(52) U.S. Cl.
CPC ........ *A61K 31/7004* (2013.01); *A61K 9/1075* (2013.01); *A61K 31/351* (2013.01); *A61K 31/4192* (2013.01); *A61K 31/7016* (2013.01); *A61K 31/7056* (2013.01); *A61K 31/724* (2013.01); *A61P 11/00* (2018.01); *A61P 31/00* (2018.01); *A61K 31/43* (2013.01); *A61K 31/7036* (2013.01); *A61K 31/7048* (2013.01); *A61K 45/06* (2013.01)

(58) Field of Classification Search
CPC ............ A61K 31/7004; A61K 31/7056; A61K 31/724; A61K 31/43
See application file for complete search history.

(56) References Cited

U.S. PATENT DOCUMENTS
2012/0165277 A1    6/2012   Leffler et al.

FOREIGN PATENT DOCUMENTS
WO    2018/022624 A1   2/2018

OTHER PUBLICATIONS
Written Opinion of the International Searching Authority for PCT/US17/43739; dated Oct. 13, 2017; 7 pages.
(Continued)

*Primary Examiner* — San Ming R Hui
(74) *Attorney, Agent, or Firm* — Morgan, Lewis & Bockius LLP

(57) ABSTRACT

Galectin 3 inhibitors and methods for treating sepsis using the same are provided herein.

24 Claims, 19 Drawing Sheets
Specification includes a Sequence Listing.

W031-9 (Lactose azide precursor; Galβ1,4Glc)
100 mM in 1x PBS

Exact Mass: 499.201
Molecular Weight: 499.470

W028-44 (GalNAc azide precursor)
100 mM in 1x PBS

Exact Mass: 378.175
Molecular Weight: 378.382

T antigen monovalent (TFD azide precursor; Galβ1,3GalNAc)
100 mM in 1x PBS

Exact Mass: 540.228
Molecular Weight: 540.523

Related U.S. Application Data

(60) Provisional application No. 62/366,203, filed on Jul. 25, 2016.

(56) References Cited

OTHER PUBLICATIONS

International Search Report for PCT/US17/43739; dated Oct. 13, 2017; 4 pages.
Andre et al.; "Persubstituted Cyclodextrin-Based Glycoclusters as Inhibitors of Protein-Carbohydrate Recognition Using Purified Plant and Mammalian Lectins and Wild-Type and Lectin-Gene-Transfected Tumor Cells as Targets", Bioconjugate Chem. 2004. vol. 15(1), pp. 87-98.
Benito et al.; "Optimizing Saccharide-Directed Molecular Delivery to Biological Receptors: Design, Synthesis, and Biological Evaluation of Glycodendrimer-Cyclodextrin Conjugates", J. Am. Chem. Soc. 2004. vol. 126, pp. 10355-10363, 9 pages.
Camby et al.; "Galectin-1: a small protein with major functions", Glycobiology vol. 16 No. 11 pp. 137R-157R, 2006 doi:10.1093/glycob/cwl025, Advance Access publication on Jul. 13, 2006; 21 pages.
Farnworth et al.; "Galectin-3 Reduces the Severity of Pneumococcal Pneumonia by Augmenting Neutrophil Function", The American Journal of Pathology, vol. 172, No. 2, Feb. 2008, DOI: 10.2353/ajpath.2008.070870; 11 pages.
Martinez et al.; "Cyclodextrin-based multivalent glycodisplays:covalent and supramolecular conjugates to assess carbohydrate-protein interactions", Chem. Soc. Rev. 2013. vol. 42, pp. 4746-4773.
Nita-Lazar et al.; "Desialylation of airway epithelial cells during influenza virus infection enhances pneumococcal adhesion via galectin binding", Mol Immunol. May 2015, 65(1): 1-16. doi:10.1016/j.molimm.2014.12.010; 37 pages.
Nita-Lazar et al.; "Galectins regulate the inflammatory response in airway epithelial cells exposed to microbial neuraminidase by modulating the expression of SOCS1 and RIG1*", Mol Immunol. Dec. 2015, 68(2 0 0): 194-202. doi:10.1016/j.molimm.2015.08.005.; 19 pages.
Pauli et al.; "Influenza A Virus Inhibits Type I IFN Signaling via NF-kBDependent Induction of SOCS-3 Expression", PLoS Pathog 4(11): e1000196. doi:10.1371/journal.ppat.1000196; 15 pages.
Pothlichet et al.; "Cutting Edge: Innate Immune Response Triggered by Influenza A Virus Is Negatively Regulated by SOCS1 and SOCS3 through a RIG-I/IFNAR1-Dependent Pathway", J Immunol 2008, 180:2034-2038, doi: 10.4049/immunol.180.4.2034, http://www.jimmunol.org/content/180/4/2034; 6 pages.
Rabinovich et al.; "Recombinant Galectin-1 and Its Genetic Delivery Suppress Collagen-induced Arthritis via T Cell Apoptosis", 1999, J. Exp. Med. 190:385-397; 13 pages.
Rabinovich et al.; "Conveying glycan information into T-cell homeostatic programs: a challenging role for galectin-1 in inflammatory and tumor microenvironments", Immunological Reviews 2009, vol. 230: 144-159; 16 pages.
Ramierz-Martinez et al.; "Seasonal and pandemic influenza H1N1 viruses induce differential expression of SOCS-1 and RIG-I genes and cytokine/chemokine production in macrophages", Cytokine. Apr. 2013, 62(1): 151-159. doi:10.1016/j.cyto.2013.01.018.; 18 pages.
Santucci et al.; "Galectin-1 Suppresses Experimental Colitis in Mice", Gastroenterology 2003;124:1381-1394; 14 pages.
Sato et al.; "Role of Galectin-3 as an Adhesion Molecule for Neutrophil Extravasation During Streptococcal Pneumonia", J Immunol 2002; 168:1813-1822; 11 pages.
Toscano et al.; "Galectin-1 Suppresses Autoimmune Retinal Disease by Promoting Concomitant Th2- and T Regulatory-Mediated Anti-Inflammatory Responses", J Immunol 2006, 176:6323-6332; 11 pages.
Toscano et al.; "Nuclear factor (NF)-kB controls expression of the immunoregulatory glycan-binding protein galectin-1", Molecular Immunology 48 (2011) 1940-1949; 10 pages.
Vasta et al.; "Roles of galectins in infection", Nat Rev Microbiol. Jun. 2009, 7(6): 424-438; 32 pages.
Wang et al.; "Design and synthesis of glycoprotein-based multivalent glycoligands for influenza hemagglutinin and human galectin-3", Bioorg Med Chem. Apr. 1, 2013, 21(7): 2037-2044; 16 pages.

W031-9 (Lactose azide precursor; Galβ1,4Glc)
100 mM in 1x PBS

Exact Mass: 499.201
Molecular Weight: 499.470

W028-44 (GalNAc azide precursor)
100 mM in 1x PBS

Exact Mass: 378.175
Molecular Weight: 378.382

T antigen monovalent (TFD azide precursor; Galβ1,3GalNAc)
100 mM in 1x PBS

Exact Mass: 540.228
Molecular Weight: 540.523

Multivalent inhibitor A

W031-11 (GaNAc-βCyclodextrin conjugate)
10 mM in 1X PBS

Exact Mass: 4334.891
Molecular Weight: 4337.375

Multivalent inhibitor B

Lactose-βCyclodextrin conjugate

Exact Mass: 5182.075
Molecular Weight: 5184.991

Multivalent inhibitor C

TFD-βCyclodextrin conjugate

Exact Mass: 5469.260
Molecular Weight: 5472.362

Bi-antennary N-glycan

Tri-antennary N-glycan

Tetra-antennary N-glycan

○ Gal  ● Man  ■ GlcNAc

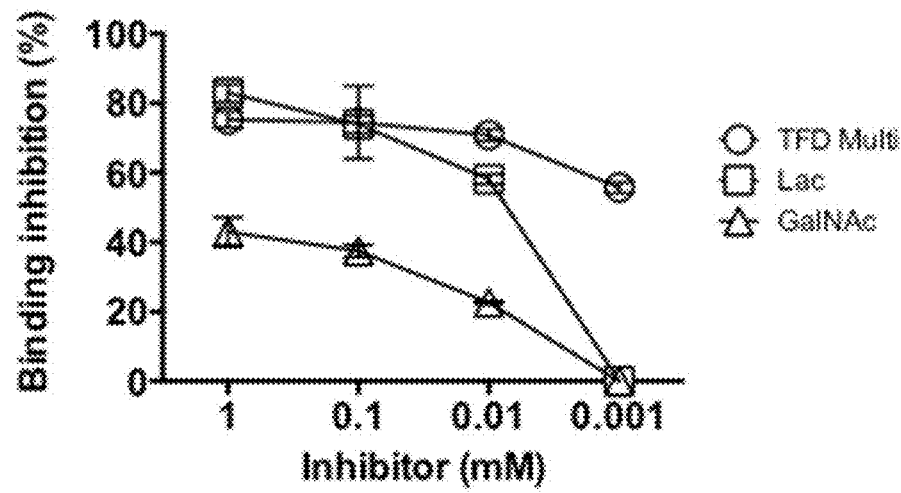
Fig. 14A
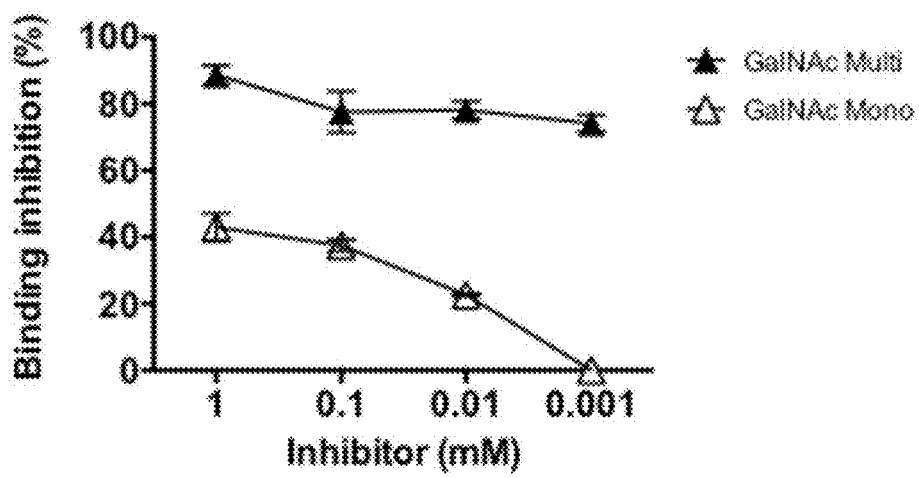
Fig. 14B
Fig. 14

INHIBITION OF GALECTIN 3 BINDING TO THE AIRWAY EPITHELIAL SURFACE TO TREAT OR PREVENT SEPTIC SHOCK RESULTING FROM INFLUENZA AND SUBSEQUENT PNEUMOCOCCAL PNEUMONIA INFECTION

CROSS-REFERENCE TO RELATED APPLICATIONS

This application is a Continuation-in-Part of, and claims the benefit of priority of, International Application No. PCT/US 17/43739, filed Jul. 25, 2017, and claims the benefit of priority of U.S. Provisional Application No. 62/366,203, filed Jul. 25, 2016, the entirety of which are incorporated herein by reference.

GOVERNMENT LICENSE RIGHTS

This invention was made with government support Grant No. GM070589 awarded by the National Institutes of Health. The government has certain rights in the invention.

FIELD OF THE INVENTION

The invention described herein relates generally to compositions and methods for treating or preventing sepsis and more particularly, but not exclusively, to mono- or oligo-saccharide-cyclodextrin conjugates that inhibit galectin 3 binding and signaling activity as therapeutics for treating or preventing sepsis.

BACKGROUND OF THE INVENTION

The rapid onset and in some cases, catastrophic outcome of influenza pandemics has revealed an urgent need to gain further insight into the airway innate immune response to infectious challenge. Influenza patients frequently display increased susceptibility to *Streptococcus pneumoniae* co-infection and sepsis, the prevalent cause of mortality during influenza pandemics, but the detailed mechanisms by which an influenza infection predisposes patients to suffer pneumococcal pneumonia and ensuing sepsis are not fully understood.

Nevertheless, there is an urgent need in the field for therapeutics and methods of treating or preventing sepsis in patients, which results from influenza.

SUMMARY OF THE INVENTION

The invention described herein meets the needs in the field by providing mono- and oligo-saccharide-cyclodextrin conjugates that may be used to treat or prevent sepsis in a patient in need thereof. In some embodiments, sepsis may be the result of pneumococcal pneumonia in the patient. In some embodiments, the pneumococcal pneumonia may be the result of influenza in the patient.

In some embodiments, the invention may include methods for treating or preventing septic shock in patients suffering from pneumococcal pneumonia after influenza infection. The methods may include inhibiting the binding of galectin 3 to the airway epithelial surface by administering to the respiratory tract (e.g., via an aerosol) one or more high affinity inhibitors of galectin 3. In some embodiments, the inhibitor prevents the binding of galectin 3 present in the bronchoalveolar space to the airway epithelial surface, which prevents the downregulation of expression of SOCS and RIG1 and prevents the hypercytokinemia resulting from the dysregulation of expression and release of pro- and anti-inflammatory cytokines, thereby preventing sepsis and septic shock.

In an embodiment, the invention includes a galectin 3 inhibitor of formula I, II, or III:

(I)

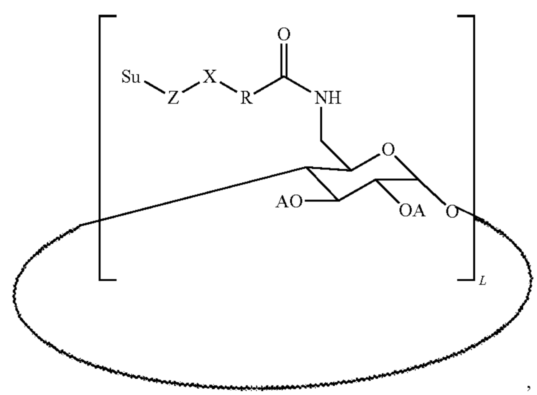

, (II)

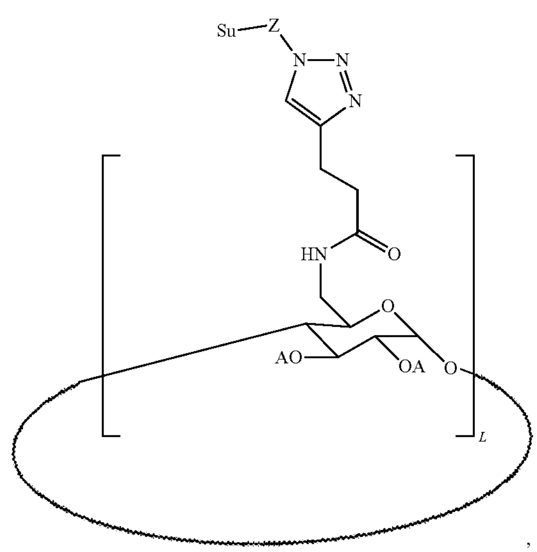

, or

-continued (III)

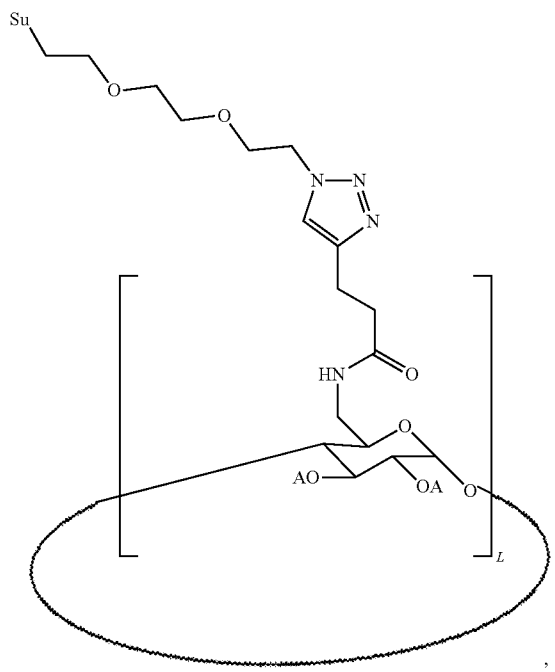

wherein Su may be a monosaccharide, disaccharide, or oligosaccharide moiety;

L may be an integer of 6, 7, or 8;

R may be a bond or a substituent selected from the group consisting of —(CH$_2$)$_n$—, —(CH$_2$CH$_2$O)$_n$—, —(CH$_2$CH$_2$CH$_2$O)$_n$—, optionally substituted -(alkyl)$_n$-, and optionally substituted -(alkoxy)$_n$-, wherein n is an integer of 1 to 20;

A may be H or —C(O)—(CH$_2$)$_k$—CH$_3$, wherein k is an integer of 3 to 7;

X may be a bond or triazolyl;

Z may be a bond or a substituent selected from the group consisting of substituted or unsubstituted alkyl, heteroalkyl, alkoxy, -alkylalkoxy-, -alkoxyalkyl-, -alkyl-(alkoxy)$_m$-, and -(alkoxy)$_m$-alkyl-, wherein m is independently an integer of 1 to 20; and a pharmaceutically acceptable salt thereof.

In some embodiments of the invention, L is 7.

In some embodiments of the invention, A is —C(O)—(CH$_2$)$_k$—CH$_3$, where k is an integer of 4 to 6. In some embodiments, k is 4.

In some embodiments of the invention, A is H.

In some embodiments of the invention, Su is a monosaccharide moiety.

In some embodiments of the invention, the monosaccharide moiety is

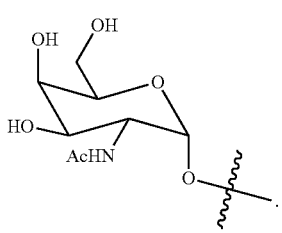 [SMILES: *OC1OC(CO)C(O)C(O)C1NC(C)=O]

In some embodiments of the invention, Su may be a disaccharide moiety.

In some embodiments of the invention, the disaccharide moiety may be

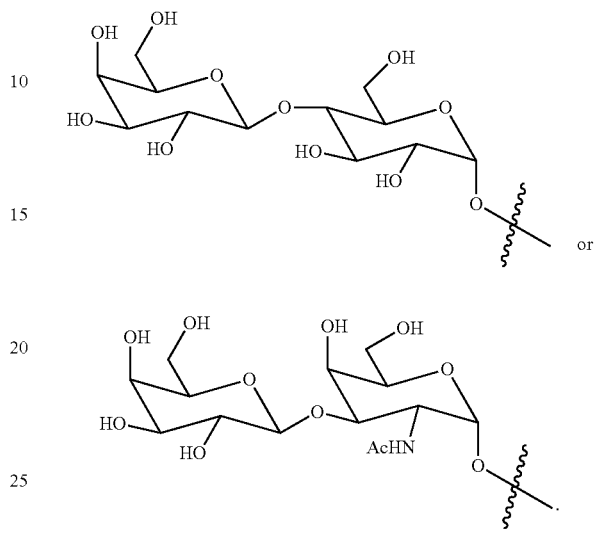

or

In some embodiments of the invention, the disaccharide moiety may be

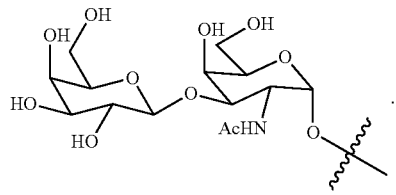 [SMILES: *OC1OC(CO)C(O)C(OC2OC(CO)C(O)C(O)C2O)C1NC(C)=O]

In some embodiments of the invention, Su may be an oligosaccharide moiety.

In some embodiments of the invention, the oligosaccharide moiety may be a bi-antennary N-glycan, a tri-antennary N-glycan, or a tetra-antennary N-glycan.

In some embodiments of the invention, the bi-antennary N-glycan, tri-antennary N-glycan, or tetra-antennary N-glycan may be of the formula IV, V, or VI, respectively:

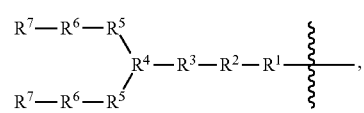
(IV)

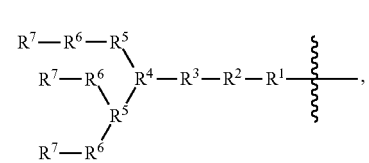
(V)

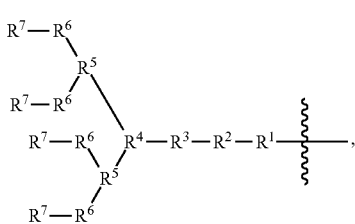

-continued (VI)

wherein $R^1$ may be a bond or Asn (asparagine);

$R^2$ and $R^3$ may be N-acetylglucosamine (GlcNAc);

$R^4$ and $R^5$ may be mannose; and each $R^6$ and $R^7$ may be independently selected from the group consisting of N-acetylglucosamine (GlcNAc), N-acetylgalactosamine (GalNAc), glucose, and galactose.

In some embodiments of the invention, the oligosaccharide moiety may be a bi-antennary N-glycan of formula (IV):

wherein $R^1$ may be a bond;

$R^2$ and $R^3$ may be GlcNAc;

$R^4$ and $R^5$ may be mannose;

$R^6$ may be GlcNAc; and $R^7$ may be galactose.

In some embodiments of the invention, the oligosaccharide moiety may be a tri-antennary N-glycan of formula (V):

wherein $R^1$ may be a bond;

$R^2$ and $R^3$ may be GlcNAc;

$R^4$ and $R^5$ may be mannose;

$R^6$ may be GlcNAc; and $R^7$ may be galactose.

In some embodiments of the invention, the oligosaccharide moiety may be a tetra-antennary N-glycan of formula (VI):

wherein $R^1$ may be a bond;

$R^2$ and $R^3$ may be GlcNAc;

$R^4$ and $R^5$ may be mannose;

$R^6$ may be GlcNAc; and $R^7$ may be galactose.

In some embodiments of the invention, one or more lipid moieties may be introduced at the rim of the secondary hydroxyl groups of the cyclodextrin, so that self-assembled micelles may be formed to add another level of multivalency and to further enhance galectin inhibitory efficacy.

In some embodiments of the invention, R may be $-(CH_2)_m-$, and m may be an integer of 1 to 3, or 2.

In some embodiments of the invention, R may be $-(CH_2)_2-$.

In some embodiments of the invention, X may be

In some embodiments of the invention, Z may be a substituted or unsubstituted -alkyl-(alkoxy)$_{m'}$- or -(alkoxy)$_{m'}$- alkyl-, wherein m' may be an integer of 1 to 20.

In some embodiments of the invention, Z may be -alkyl-$(CH_2O)_{k'}-$, -alkyl-$(CH_2CH_2O)_{k'}-$, -alkyl-$(CH_2CH_2CH_2O)_{k'}-$, $-(CH_2O)_{k'}$-alkyl-, $-(CH_2CH_2O)_{k'}$-alkyl-, or $-(CH_2CH_2CH_2O)_{k'}$-alkyl-, and k' may be an integer of 1 to 5. In some embodiments, k' may be an integer of 2 to 4. In some embodiments, k' may be an integer of 2.

In some embodiments of the invention, Z may be $-(CH_2CH_2O)_{k'}$-alkyl-, and k' may be an integer of 1 to 5, or 2 to 4, or 2.

In an embodiment, the invention includes a pharmaceutical formulation for treating or preventing septic shock by inhibiting galectin 3 activity in a patient in need thereof. The pharmaceutical formulation may include a therapeutically effective amount of a galectin 3 inhibitor as described herein, or a pharmaceutically acceptable salt thereof, and a pharmaceutically acceptable carrier.

In some embodiments, the pharmaceutical formulation may be provided in unit dosage form selected from the group consisting of a liquid dosage form and a solid dosage form.

In an embodiment, the invention may include a method for treating or preventing septic shock by inhibiting galectin 3 activity in a patient in need thereof. The method may include administering a therapeutically effective amount of a galectin 3 inhibitor described herein, or a pharmaceutically acceptable salt thereof.

In some embodiments of the methods described herein, the patient may have pneumococcal pneumonia.

In some embodiments of the methods described herein, administering the therapeutically effective amount of the galectin 3 inhibitor includes oral or intranasal administration.

In some embodiments of the methods described herein, administering the therapeutically effective amount of the galectin 3 inhibitor includes oral or intranasal administration via inhalation.

In some embodiments of the methods described herein, inhibiting galectin 3 activity includes inhibiting binding of galectin 3 to an airway epithelial surface of the patient.

In some embodiments, the methods described herein may include the administration of a therapeutically effective amount of an additional active agent to the patient. In some embodiments, the additional active agent comprises an antibacterial agent selected from the group consisting of cefazolin, nafcillin, vancomycin, cefoxitin, neomycin plus erythromycin, penicillin G, trimethoprim plus sulfamethoxazole, and clindamycin or clindamycin plus gentamycin or tobramycin.

In an embodiment, the invention includes a galectin 3 inhibitor micelle comprising a plurality of compounds of formula I, II, or III, as described herein. In some embodiments, such micelles may be prepared in vitro and delivered as galectin 3 inhibitors according to the methods and pharmaceutical formulations described herein.

BRIEF DESCRIPTION OF THE DRAWINGS

The foregoing summary, as well as the following detailed description of the invention, will be better understood when read in conjunction with the appended drawings.

FIG. 1 illustrates exemplary monovalent galectin inhibitors of the invention that are azide precursors used for preparing P-cyclodextrin conjugates.

FIG. 2 illustrates Multivalent Inhibitor A, which is a GalNAc-βCyclodextrin conjugate.

FIG. 3 illustrates Multivalent Inhibitor B, which is a lactose-βCyclodextrin conjugate.

FIG. 4 illustrates Multivalent Inhibitor C, which is a TFD-βCyclodextrin conjugate.

FIG. 5 illustrates the exposure of lung carcinoma A549 cells to microbial neuraminidase and extracellular Gal1 and Gal3 modulates expression of SOCS1 and RIG1. Total RNA was extracted from A549 control (Ctrl) or neuraminidase (*Arthrobacter ureafaciens* and *Clostridium perfringens*) treated cells (NeuK) incubated in presence or absence of 15 µg/ml exogenous rhGal1 or rhGal3 for 1 h. (Panel A) SOCS1 transcript level was analyzed by RT-PCR. (Panel B) RIG1 transcript levels were analyzed by RT-PCR. Bar graphs show the fold change in mRNA expression levels in neuraminidase treated cells as well as galectin treated cells in comparison with control cell without neuraminidase and galectin treatment (Ctrl) after normalized to β-actin. All studies represent one of three independent experiments. $*p<0.05$; $**p<0.001$, non paired Student's t test.

FIG. 6 illustrates that activation of regulatory signaling pathways in A549 cells is modulated by exposure to microbial neuraminidase and extracellular Gal1 and Gal3. Total cell lysates were extracted from A549 control (Ctrl) or neuraminidase-treated cells (NeuK) incubated in the presence or absence of 15 µg/ml rhGal1 and rhGal3, and subject to 4 to 20% gradient SDS-PAGE. Total and phosphorylated protein levels of Integrin beta3 (INTb3) (Panel E), ERK (Panel A), AKT (Panel B), p38 MAPK (Panel C), STAT1 (Panel D) and NF-κB (Panel F) were assessed by western blot. Bar graphs show the fold changes of phosphorylation levels in treated cells in comparison with control cells after normalization to total proteins. Shown images and the bar graphs are representative of data from at least two independent experiments. $*p<0.05$; $**p<0.001$, non paired Student's t test.

FIG. 7 illustrates the levels of cytokines released by A549 cells. A549 control (Ctrl) or neuraminidase treated (NeuK) cells were stimulated in presence or absence of 15 µg/ml exogenous rhGal1 and rhGal3. The cytokines (IFN-γ, TNF-α, IL-1β, IL-6, IL-8, IL-10, IL-12 and IL-15) released to the culture medium was measured by MSD multi-spot assay. $*p<0.05$; $**p<0.001$, non paired Student's t test.

Figure 13:
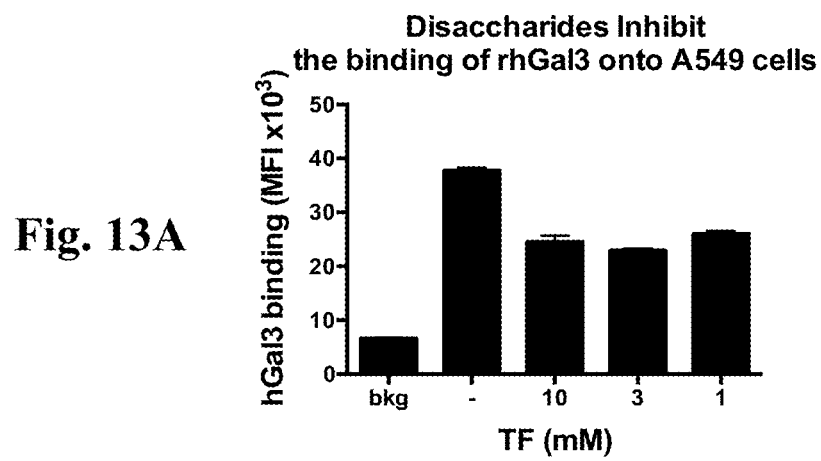
Figure 13:
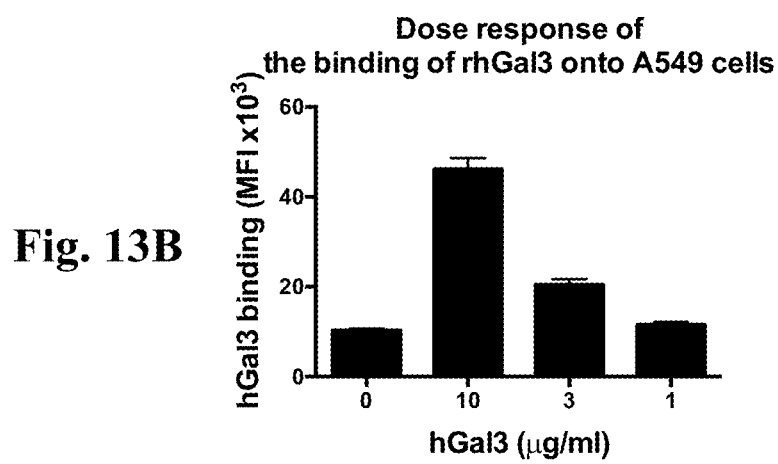
Figure 13:
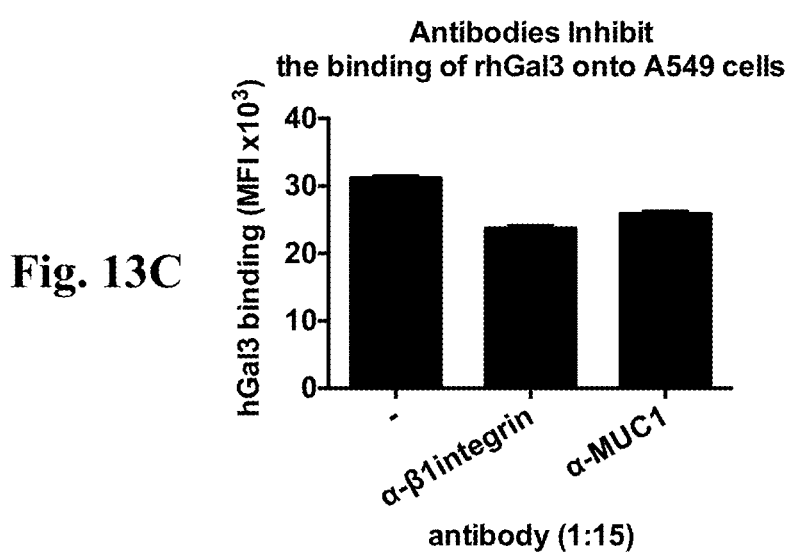

FIG. 13 illustrates the binding of rhGal3 to A549 cells and inhibition by natural and synthetic inhibitors, and antibodies against MUC1 and β1integrin partially inhibit Gal3 binding onto A549 cells. FIG. 13A: mean fluorescent intensity (MFI) with SE of each sample; FIG. 13B: dose-dependent binding onto A549 cells was observed; FIG. 13C: both antibodies tested partially inhibit rhGal3 binding.

FIG. 14 illustrates monovalent vs multivalent inhibitors of Gal3 binding; FIG. 14A: disaccharides (TFD and Lac) are better than GalNAc, and TFD has better inhibition capacity at the lower concentrations; FIG. 14B: A549 cells were incubated with Gal3 pre-mixed with different concentration of monovalent (GalNAc Mono) or multivalent compounds of N-Acetylgalactosamine.

Figure 15B:
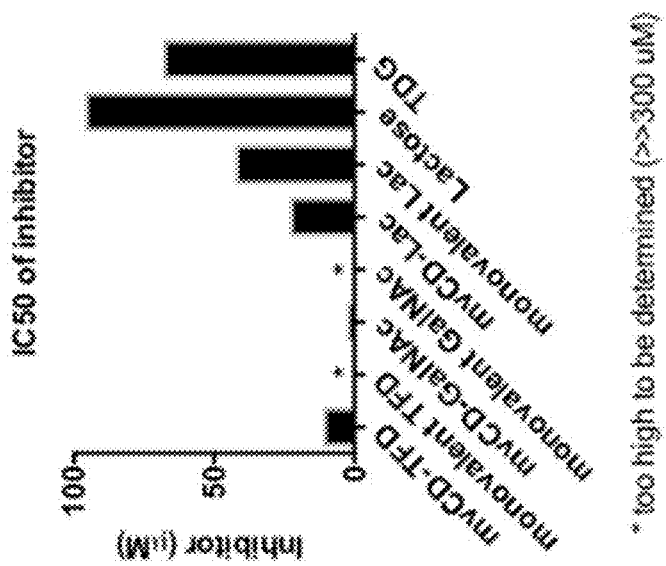
Figure 15A:
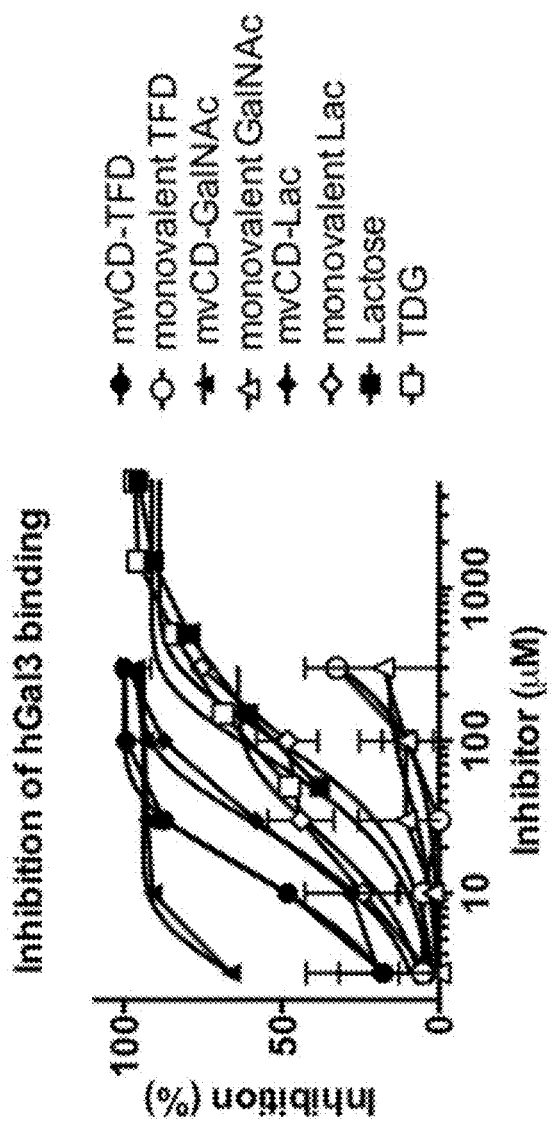

FIG. 15 illustrates the IC50 of multivalent and monovalent compounds. FIG. 15A: the % inhibition as (original concentration-relative concentration)/original concentration×100);

FIG. 15B: % inhibition with different inhibitors drawn over concentration of inhibitors to calculate their IC50.

Figure 16A:
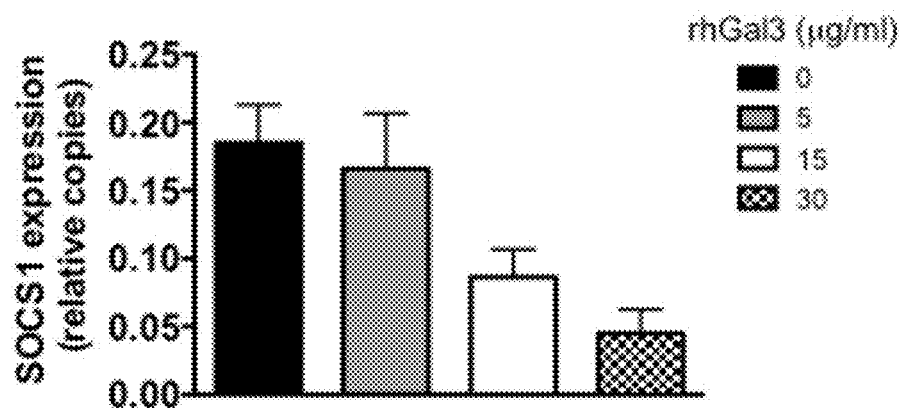
Figure 16B:
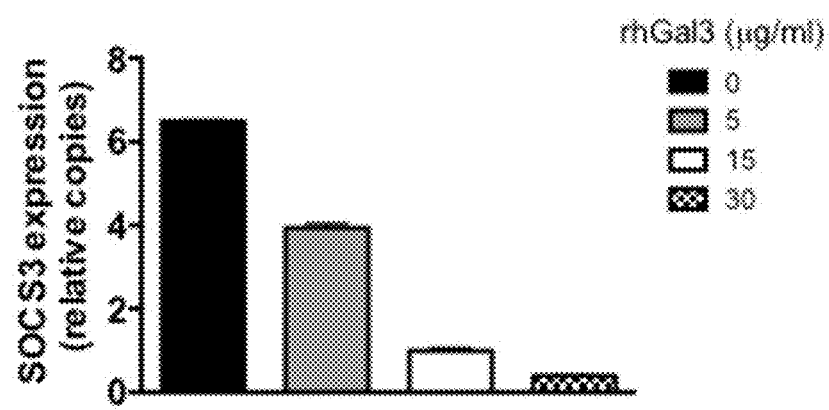
Figure 16C:
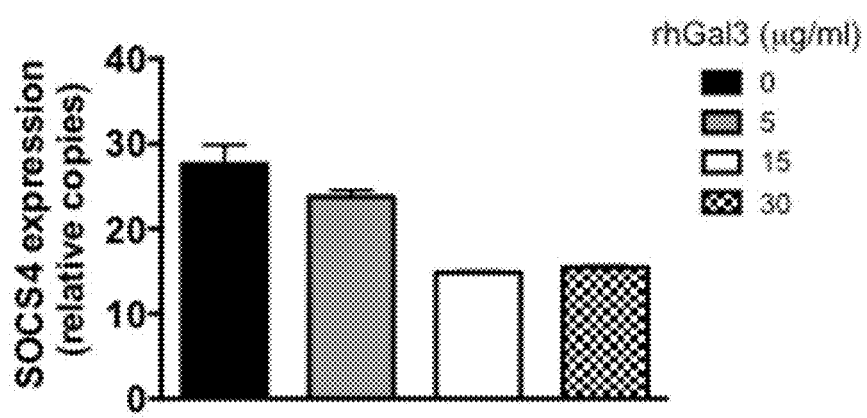

FIG. 16 illustrates the downregulation of SOCS expression by Gal3. FIG. 16A: SOCS1: FIG. 16B: SOCS3; FIG. 16C: SOCS4.

Figure 17A:
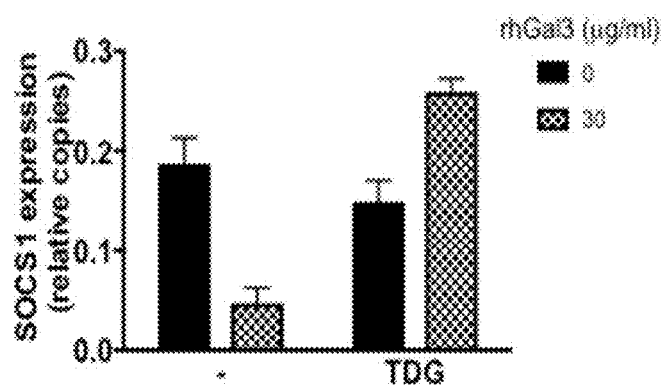
Figure 17B:
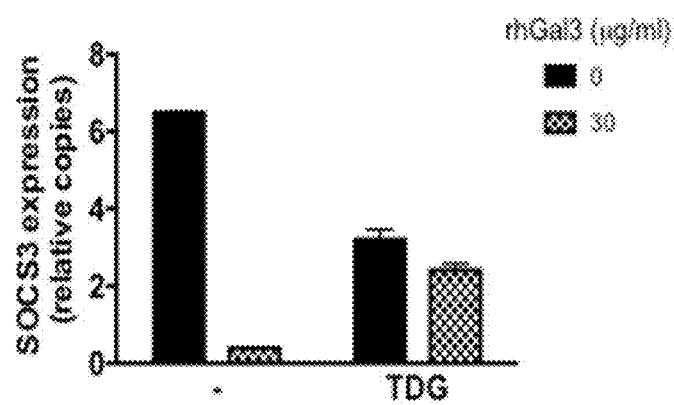
Figure 17C:
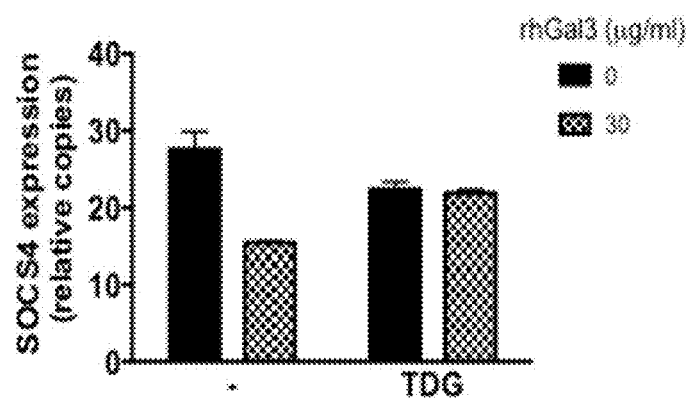

FIG. 17 illustrates that while disaccharide alone has some positive effect in SOCS expression, the mixture of galectin with disaccharide offset all the galectin's effect in suppressing SOCS expression, showing similar expression level as disaccharide alone (FIG. 17B: SOCS3, FIG. 17C: SOCS4) or slightly higher (FIG. 17A: SOCS1).

Figure 18:
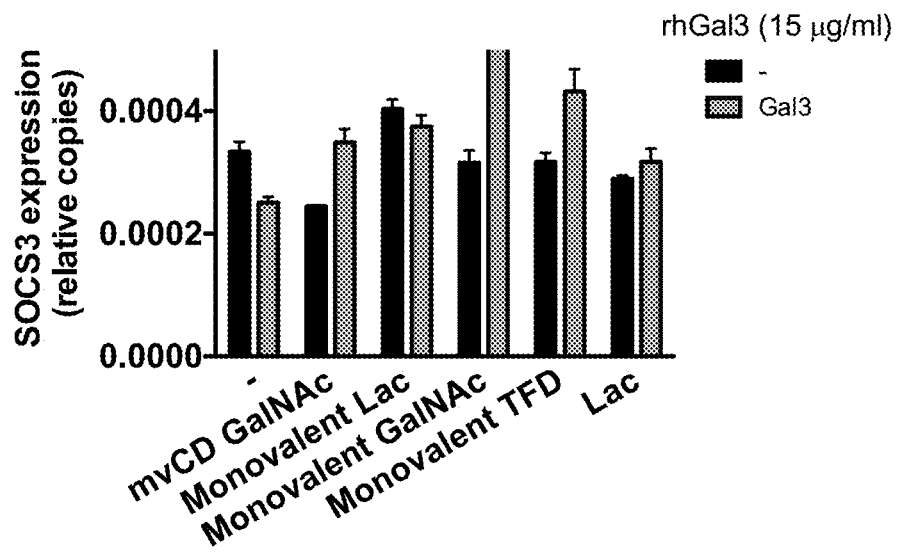

FIG. 18 illustrates prevention of downregulation of SOCS3 (FIG. 18).

Figure 19A:
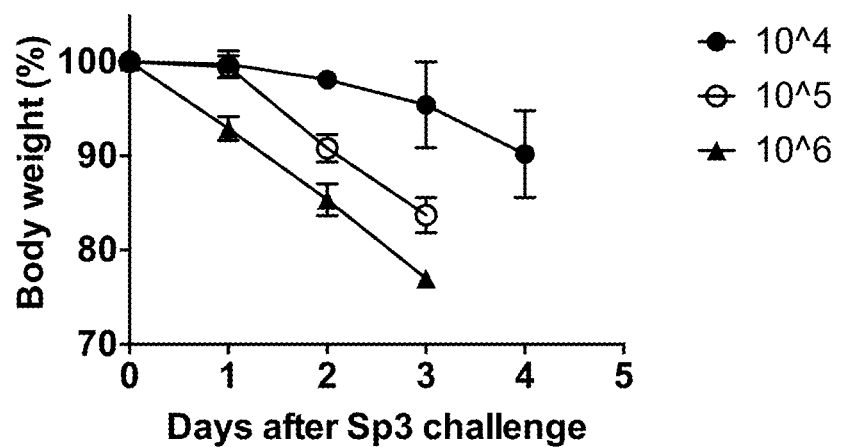
Figure 19B:
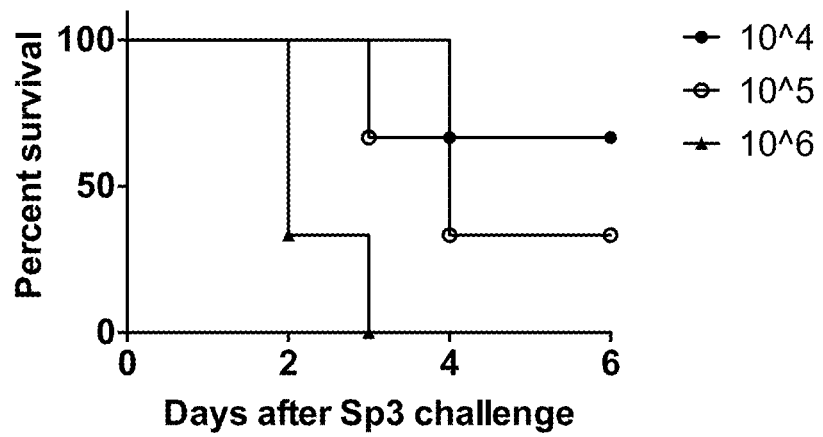

FIG. 19 illustrates the determination of lethal and sublethal Sp3 dose; heterozygous littermates were challenged with Sp3 from $10^4$ to $10^6$ (3 mice each group) and the survival (FIG. 19B) and body weight (FIG. 19A) were followed for up to 6 days.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least galectin 3 inhibitor) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The terms "active pharmaceutical ingredient" and "drug" include the compounds described herein and, more specifically, the compounds described by formula (I), formula (II), and/or formula (III). The terms "active pharmaceutical ingredient" and "drug" may also include those compounds described herein that inhibit and/or otherwise modulate galectin 3 activity.

The terms "galectin 3 inhibitors," "galectin 3 inactivators," and "galectin 3 antagonists" refer to inhibitory molecules, identified using in vitro and in vivo assays for galectin 3 binding or signaling, e.g., ligands, antagonists, and their homologs and mimetics. Galectin 3 inhibitors may partially or totally block carbohydrate binding, decrease, prevent, delay activation, inactivate, desensitize, or down regulate the signaling activity of galectin 3. In some embodiments, the terms "galectin 3 inhibitors," "galectin 3 inactivators," and "galectin-3 antagonists" include the compounds described herein and, more specifically, the compounds described by formula I, formula II, and/or formula III. In some embodiments of the invention, "galectin 3 inhibitors," "galectin 3 inactivators," and "galectin-3 antagonists" may include micelles prepared from a plurality of compounds described by formula I, formula II, and/or formula III. In some embodiments, the inhibitors directly or indirectly bind to galectin 3. Galectin 3 ligand inhibitors may also include, but are not limited to, galactose, galactoside, glycoconjugates that bind to galectin 3 (e.g., a glyco lipid, glycopeptide, or proteoglycan), saccharides (e.g., monosaccharides, disaccharides, trisaccharides, polysaccharides, or oligosaccharides such as lactose, tetrasaccharide, beta-galactosidase, or derivatives thereof), glycodendrimer, N-acetyl lactosamine, or a derivative thereof (e.g., C3' amide, sulfonamide, or urea derivative) and pectins. The term "selective galectin 3 inhibitor" refers to galectin 3 inhibitors of the invention that selectively prevent the binding of galectin 3 over other galectin proteins (e.g., galectin 1).

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., inhibition of galectin 3 binding). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition). As used herein, the terms "prevent," "preventing," and/or "prevention" may refer to reducing the risk of developing a disease, disorder, or pathological condition.

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule. In some embodiments, the biological molecules modulated by the methods and compounds of the invention to effect treatment may include galectin 3.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, H., Design of Prodrugs (1985) (Elsevier, Amsterdam). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $(C_{2-10})$alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., $(C_{2-10})$alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_{3-10}$cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a $(C_{1-6})$alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^a$, and NR$^a$R$^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "aryloxy" refers to the group —O-aryl.

The term "substituted aryloxy" refers to aryloxy wherein the aryl substituent is substituted (i.e., —O-(substituted aryl)). Unless stated otherwise specifically in the specification, the aryl moiety of an aryloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., C$_1$-C$_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl) heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d] pyrimidinyl, 6,7-dihydro-5H-cyclopenta[4,5]thieno[2,3-d] pyrimidinyl, 5,6-dihydrobenzo[h]quinazolinyl, 5,6-dihydrobenzo[h]cinnolinyl, 6,7-dihydro-5H-benzo[6,7] cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7, 8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)— R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. With regard to the sugars moieties described herein, unless specifically stated otherwise, all sugars are provided as D isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)— (optionally substituted heteroaryl) and —S(O)-(optionally substituted heterocycloalkyl).

"Sulfonyl" refers to groups that include —S($O_2$)—H, —S($O_2$)-(optionally substituted alkyl), —S($O_2$)-(optionally substituted amino), —S($O_2$)-(optionally substituted aryl), —S($O_2$)—(optionally substituted heteroaryl), and —S($O_2$)-(optionally substituted heterocycloalkyl).

"Sulfonamidyl" or "sulfonamido" refers to a —S($=$O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S($=$O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S($=$O)$_{2O}$H radical.

"Sulfonate" refers to a —S($=$O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All embodiments of the invention can, in the alternative, be more specifically defined by any of the transitional terms "comprising," "consisting essentially of," and "consisting of."

Methods of Treating Sepsis

The compounds and compositions described herein can be used in methods for treating or preventing diseases. In some embodiments, the compounds and compositions described herein can be used for treating or preventing diseases associated with the upregulation or increased secretion or activity of galectin 3 (i.e., Gal3). In some embodiments, the compounds and compositions described herein can be used for treating or preventing sepsis and/or septic shock. In some embodiments, the compounds and compositions described herein can be used for treating sepsis and/or septic shock that may be a result of pneumococcal pneumonia and which may follow influenza viral infection in a patient. In some embodiments, the compounds and compositions described herein can be used inhibiting galectin 3 upregulation or increaseed secretion or activity in airway epithelial tissues in a patient in need thereof. In some embodiments, the compounds that can be used in the methods described herein include those described by formulas I, II, and/or III.

Influenza patients frequently display increased susceptibility to bacterial infections, such as streptococcal pneumonia. Influenza co-infection with one of the prevalent pathogens, *Streptococcus pneumoniae* can lead to sepsis, which is the major cause of mortality during influenza pandemics. The synergic effect of the influenza A virus (IAV) and *S. pneumoniae* has been responsible for nearly all influenza deaths in 1918 influenza pandemic and up to 34% of 2009 pandemic influenza A. The detailed mechanisms by which an influenza infection predisposes patients to suffer pneumococcal pneumonia and progress to uncontrolled hypercytokinemia, however, are not fully understood. In a murine model, the animals that have recovered from IAV sublethal infection undergo a usually fatal uncontrolled cytokine response after challenge with *S. pneumoniae*, which closely reflects the observations in human patients. The reasons are unknown, but upon IAV infection, an antiviral response is initiated by the retinoic acid inducible gene 1 (RIG1), a helicase of the RIG-1 like receptor (RLR) family, which recognizes the cytosolic viral RNA and signals via the interferon-alpha/beta receptor 1 (IFNAR1)-dependent pathway to induce the expression and release of interferons and other cytokines. In turn, the potentially excessive production of cytokines and activation of both innate and adaptive immune mechanisms is controlled by the upregulation of expression of suppressors of cytokine signaling (SOCS) particularly SOCS1, SOCS3, and SOCS4. SOCS are a multigene family of intracellular proteins, which have been shown to regulate the responses of immune cells to the cytokines by negative regulation of the cytokine-induced JAK-STAT pathway. Most SOCS proteins are induced by cytokines, and therefore participate in a classical negative feedback loop to inhibit cytokine signal transduction. There are eight members of the SOCS family (SOCS1-8), each of which has a central SRC homology 2 (SH2) domain, an amino-terminal domain of variable length and a divergent sequence, and a carboxy-terminal 40-amino-acid domain that it is known as the SOCS box. SOCS1 protein levels, directly induced by viable microbes, are important for host defense by inhibiting both type I and type II interferon (IFN) signaling.

The cell surface glycocalyx, comprising glycoproteins, glycolipids and other glycans, plays a major role in modulation of host-pathogen interactions by encoding key information necessary for microbial adhesion and entry as well as for the induction of the ensuing immune responses by the host. The structural changes in cell surface glycans resulting from the enzymatic activity (glycosidases and glycosyltransferases) from both host and pathogen, as well as the reciprocal recognition of these carbohydrate moieties by their glycan-binding proteins, represent a dynamic interplay that can define the outcome of the host-pathogen interaction. For example, the glycoproteins hemagglutinin (HA) and neuraminidase (NA) displayed on the IAV surface play critical roles in viral adhesion and infection, as well as the release of the newly assembled virions. HA is a major viral surface glycoprotein, which initiates the infection by binding to sialic acid (SA) moieties present on the cell surface. Once the virus is internalized by endocytosis the HA is cleaved into HA1 and HA2 subunits. When the replication process is terminated, the NA facilitates the release of progeny virions that infect neighboring cells. Moreover, viral neuraminidase contributes to the increase of bacterial adhesion and dissemination by cleaving the respiratory epithelial cell sialic acids.

Among the host glycan-binding proteins, the critical roles of C-type lectins in pathogen recognition have been described in considerable detail, as well as the ensuing effector functions such as complement activation. In recent years, however, evidence has accumulated in support of key roles of galectins in defining the outcome of microbial infection. Galectins are a family of soluble β-galactoside-binding proteins that are synthesized in the cytosol and may carry out their biological roles in the nuclear compartment, cytoplasm, cell surface, and extracellular space. They are classified into three major structural types: proto-, chimera-, and tandem-repeat. Galectins are expressed and secreted to the extracellular space by various cell types, including epithelial cells, neutrophils, macrophages, dendritic cells, B and T cells. Further, a substantial body of evidence supports their critical roles both in the regulation of immune homeostasis as well as pattern recognition receptors in the recognition of glycans on the viral or bacterial surfaces. Recent evidence suggests their roles in the lung innate immune response to pneumococcal infection, although the mechanisms remain largely unknown.

It has been shown in vitro and in vivo that the expression and secretion of galectins, particularly galectin-1 (Gal1) and galectin-3 (Gal3), are modulated during IAV infection, and that the viral neuraminidase unmasks galactosyl moieties in the airway epithelia. The increased levels of galectins remaining in the bronchoalveolar space upon recovery from influenza further contribute to the increased binding of Gal3 and enhancement of pneumococcal adhesion by cross-linking the bacteria to the cell surface. Thus, it is proposed that the activity of the influenza and pneumococcal neuraminidases, which unmask galactosyl moieties on the airway epithelial cell surface, and act synergistically with the increased Gal3 and Gal1 concentrations in the bronchoalveolar space to promote galectin binding and additional pneumococcal adhesion as shown in a previous study, could also regulate the cytokine/chemokine expression and release by the airway epithelial cells and lead to the typical cytokine storm.

In some embodiments, the methods described herein may include the administration or co-administration of a therapeutically effective amount of an additional active agent. In some embodiments, the additional active agent may include cefazolin, nafcillin, vancomycin, cefoxitin, neomycin plus erythromycin, penicillin G, trimethoprim plus sulfamethoxazole, and clindamycin or clindamycin plus gentamycin or tobramycin.

In some embodiments, the additional active agent may include one or more compounds described by U.S. Pat. Nos. 8,697,862, 9,180,175, and 9,353,141 or International Patent Application Publication No. WO 2016/004093, the entirety of which are incorporated herein by reference.

Efficacy of the methods, compounds, and combinations of compounds described herein in treating, preventing and/or managing the indicated diseases or disorders can be tested using various animal models known in the art, including those described herein.

Galectin Inhibitors

In an embodiment, the compounds described herein are galectin inhibitors. In some embodiments the compounds described herein are selective galectin inhibitors in that they selectively inhibit or modulate activity of galectin 3 over galectin 1. In some embodiments, the compounds described herein are saccharide-cyclodextrin conjugates that inhibit galectin 3 activity. In some embodiments, the saccharide-cyclodextrin conjugates include those described by one or more of formulas I, II, and/or III.

In an embodiment, the invention includes a galectin 3 inhibitor of formula I, II, or III:

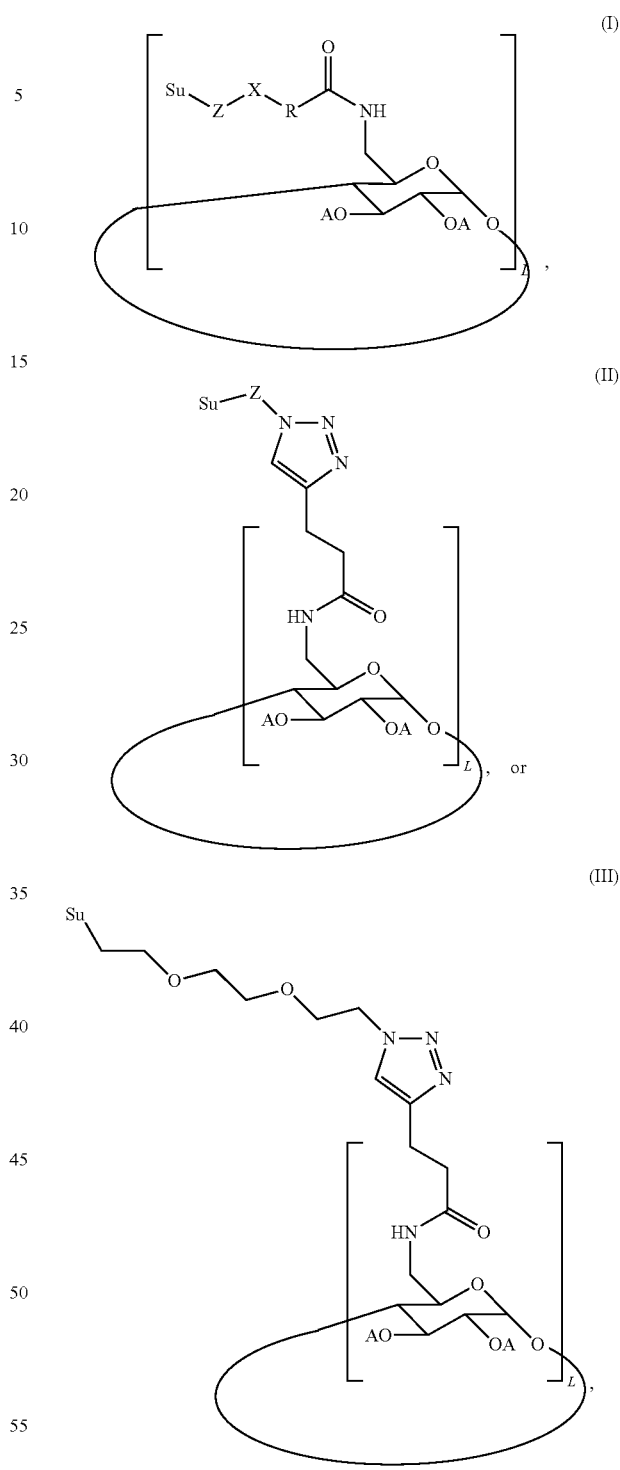

wherein Su may be a monosaccharide, disaccharide, or oligosaccharide moiety;

L may be an integer of 6, 7, or 8;

R may be a bond or a substituent selected from the group consisting of $-(CH_2)_n-$, $-(CH_2CH_2O)_n-$, $-(CH_2CH_2CH_2O)_n-$, optionally substituted -(alkyl)$_n$-, and optionally substituted -(alkoxy)$_n$-, wherein n is an integer of 1 to 20;

A may be H or —C(O)—(CH$_2$)$_k$—CH$_3$, wherein k is an integer of 3 to 7;

X may be a bond or triazolyl;

Z may be a bond or a substituent selected from the group consisting of substituted or unsubstituted alkyl, heteroalkyl, alkoxy, -alkylalkoxy-, -alkoxyalkyl-, -alkyl-(alkoxy)$_m$-, and -(alkoxy)$_m$-alkyl-, wherein m is independently an integer of 1 to 20; and a pharmaceutically acceptable salt thereof.

In some embodiments of the invention, L is 7 (i.e., β-cyclodextrin).

In some embodiments of the invention, A is —C(O)—(CH$_2$)$_k$—CH$_3$, where k is an integer of 4 to 6. In some embodiments, k is 4. In some embodiments, where A is —C(O)—(CH$_2$)$_k$—CH$_3$, and where k is an integer of 4 to 6, a plurality of galectin 3 inhibitors of formulas I, II, and/or III may form a micelle in vitro or in vivo. Where such micelles are formed in vitro, they may be collected and provided as galectin 3 inhibitors in the formulations and methods described herein.

In some embodiments of the invention, A is H.

In some embodiments of the invention, Su is a monosaccharide moiety.

In some embodiments of the invention, the monosaccharide moiety is

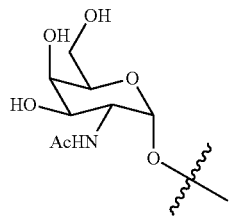

In some embodiments of the invention, Su may be a disaccharide moiety.

In some embodiments of the invention, the disaccharide moiety may be

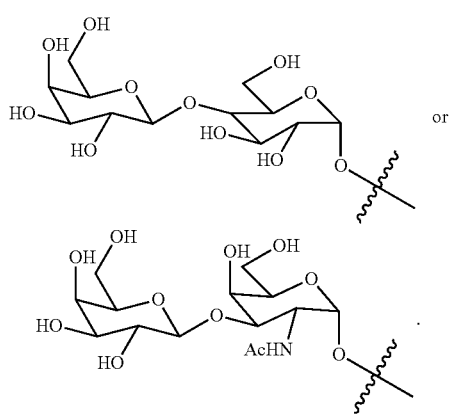

In some embodiments of the invention, the disaccharide moiety may be

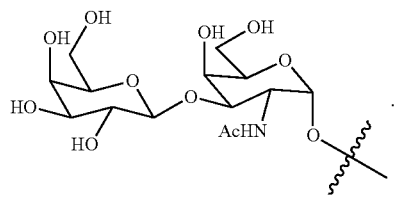 [SMILES: *OC1OC(CO)C(O)C(OC2OC(CO)C(O)C(O)C2O)C1NC(C)=O]

In some embodiments of the invention, Su may be an oligosaccharide moiety.

In some embodiments of the invention, the oligosaccharide moiety may be a bi-antennary N-glycan, a tri-antennary N-glycan, or a tetra-antennary N-glycan.

In some embodiments of the invention, the bi-antennary N-glycan, tri-antennary N-glycan, or tetra-antennary N-glycan may be of the formula IV, V, or VI, respectively:

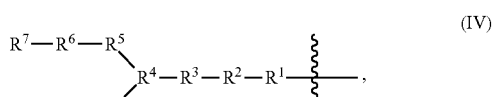

(IV)

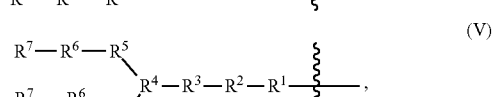

(V)

(VI)

wherein R$^1$ may be a bond or Asn (asparagine);
R$^2$ and R$^3$ may be N-acetylglucosamine (GlcNAc);
R$^4$ and R$^5$ may be mannose; and
each R$^6$ and R$^7$ may be independently selected from the group consisting of N-acetylglucosamine (GlcNAc), N-acetylgalactosamine (GalNAc), glucose, and galactose. In various embodiments, R$^2$—R$^7$ (e.g., R$^2$—R$^3$) are interconnected by glycosidic linkages.

In some embodiments of the invention, the oligosaccharide moiety may be a bi-antennary N-glycan of formula (IV):
wherein R$^1$ may be a bond;
R$^2$ and R$^3$ may be GlcNAc;
R$^4$ and R$^5$ may be mannose;
R$^6$ may be GlcNAc; and
R$^7$ may be galactose.

In some embodiments of the invention, the oligosaccharide moiety may be a tri-antennary N-glycan of formula (V):
wherein R$^1$ may be a bond;
R$^2$ and R$^3$ may be GlcNAc;
R$^4$ and R$^5$ may be mannose;
R$^6$ may be GlcNAc; and
R$^7$ may be galactose.

In some embodiments of the invention, the oligosaccharide moiety may be a tetra-antennary N-glycan of formula (VI):
wherein R$^1$ may be a bond;
R$^2$ and R$^3$ may be GlcNAc;

R⁴ and R⁵ may be mannose;
R⁶ may be GlcNAc; and
R⁷ may be galactose.

In some embodiments of the invention, one or more lipid moieties may be introduced at the rim of the secondary hydroxyl groups of the cyclodextrin, so that self-assembled micelles may be formed to add another level of multivalency and to further enhance galectin inhibitory efficacy.

In some embodiments of the invention, R may be —(CH₂)ₘ—, and m may be an integer of 1 to 3.

In some embodiments of the invention, R may be —(CH₂)₂—.

In some embodiments of the invention, X may be

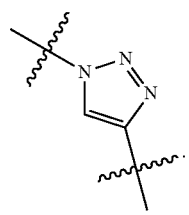 [SMILES: *c1cn(*)nn1]

In some embodiments of the invention, Z may be a substituted or unsubstituted -alkyl-(alkoxy)ₘ'- or -(alkoxy)ₘ'-alkyl-, wherein m' may be an integer of 1 to 20.

In some embodiments of the invention, Z may be -alkyl-(CH₂O)ₖ'—, -alkyl-(CH₂CH₂O)ₖ'—, -alkyl-(CH₂CH₂CH₂O)ₖ'—, —(CH₂O)ₖ'-alkyl-, —(CH₂CH₂O)ₖ'-alkyl-, or —(CH₂CH₂CH₂O)ₖ'-alkyl-, and k' may be an integer of 1 to 5.

In some embodiments of the invention, Z may be —(CH₂CH₂O)ₖ'-alkyl-, and k' may be an integer of 1 to 5.

Figure 1:
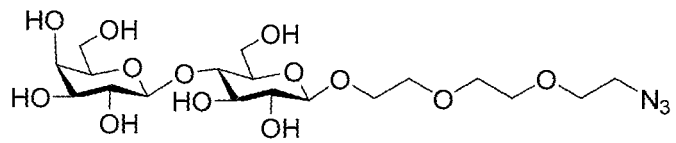
Figure 1:
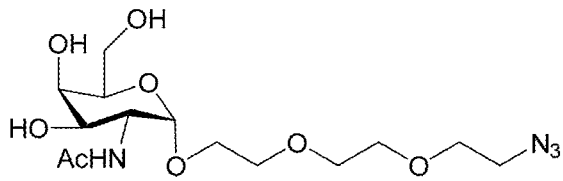
Figure 1:
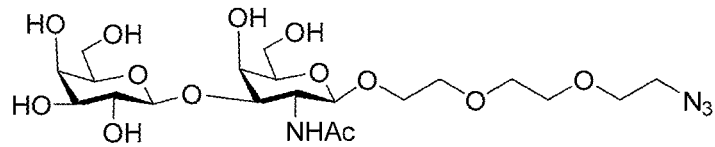

In some embodiments of the invention, the galectin 3 inhibitor may be prepared from one or more of the precursors illustrated in FIG. 1. In some embodiments, the galectin 3 inhibitor may be prepared from the lactose azide precursor of FIG. 1. In some embodiments, the galectin 3 inhibitor may be prepared from the GalNAc azide precursor of FIG. 1. In some embodiments, the galectin 3 inhibitor may be prepared from the TFD azide precursor of FIG. 1.

Figure 2:
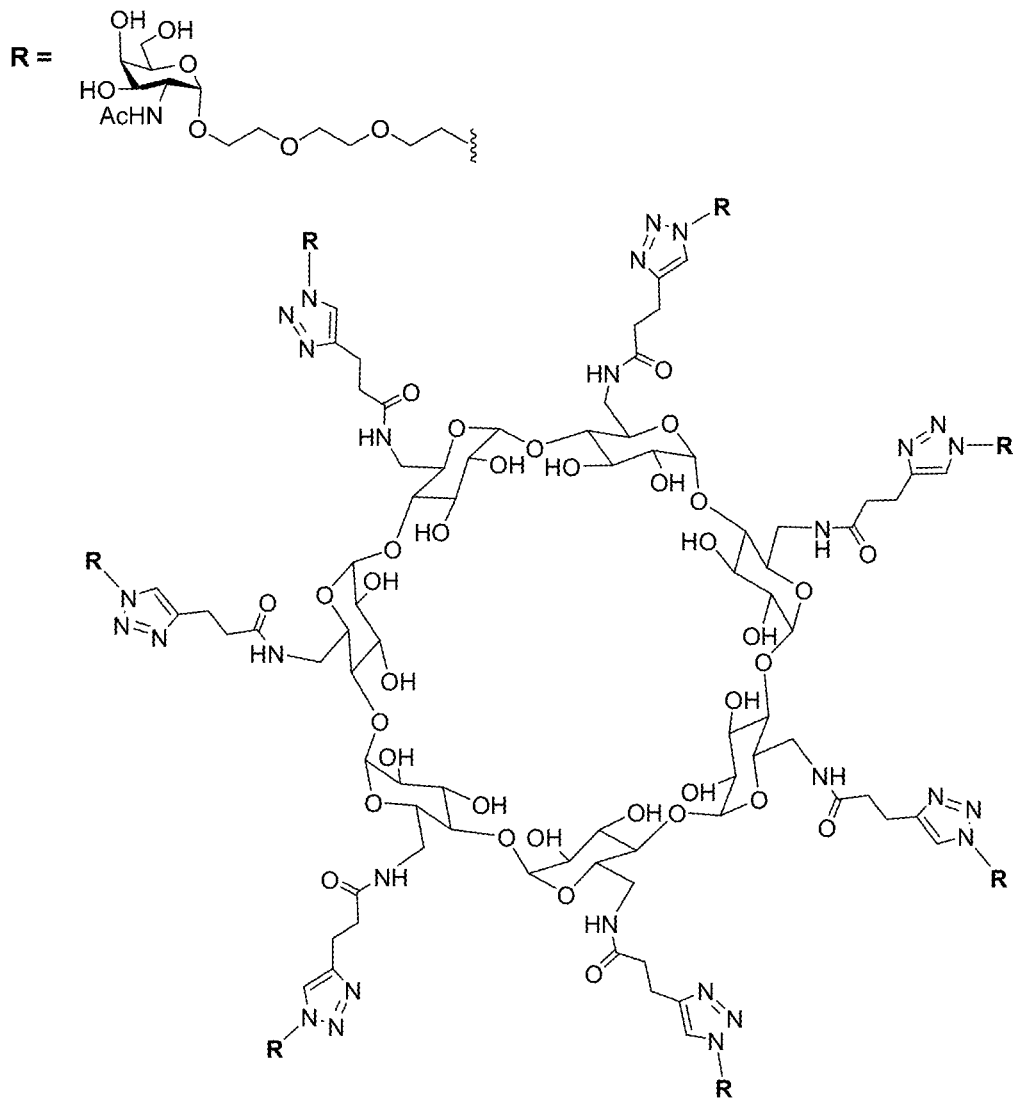

In some embodiments, the galectin 3 inhibitor may be Multivalent Inhibitor A of FIG. 2 or a pharmaceutically acceptable salt thereof.

Figure 3:
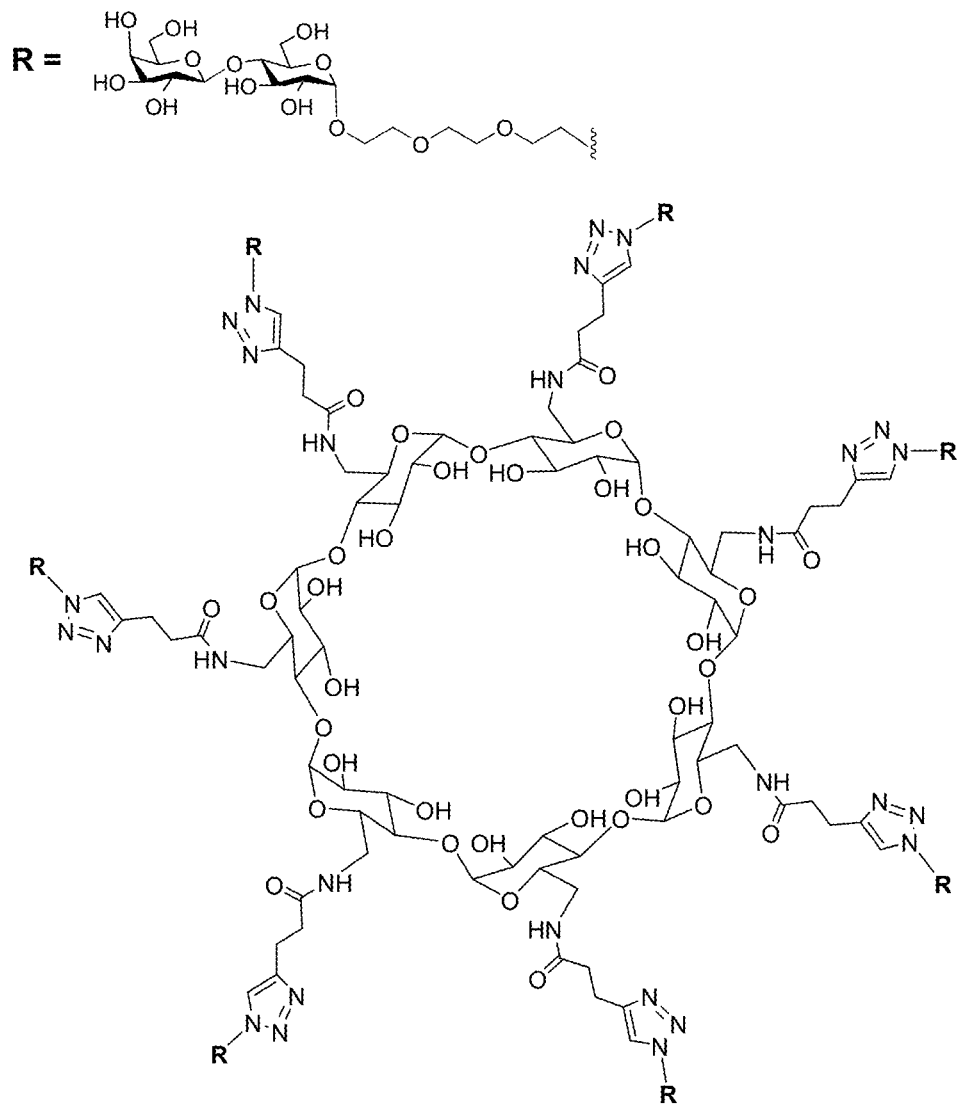

In some embodiments, the galectin 3 inhibitor may be Multivalent Inhibitor B of FIG. 3, or a pharmaceutically acceptable salt thereof.

Figure 4:
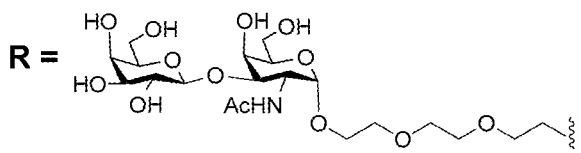
Figure 4:
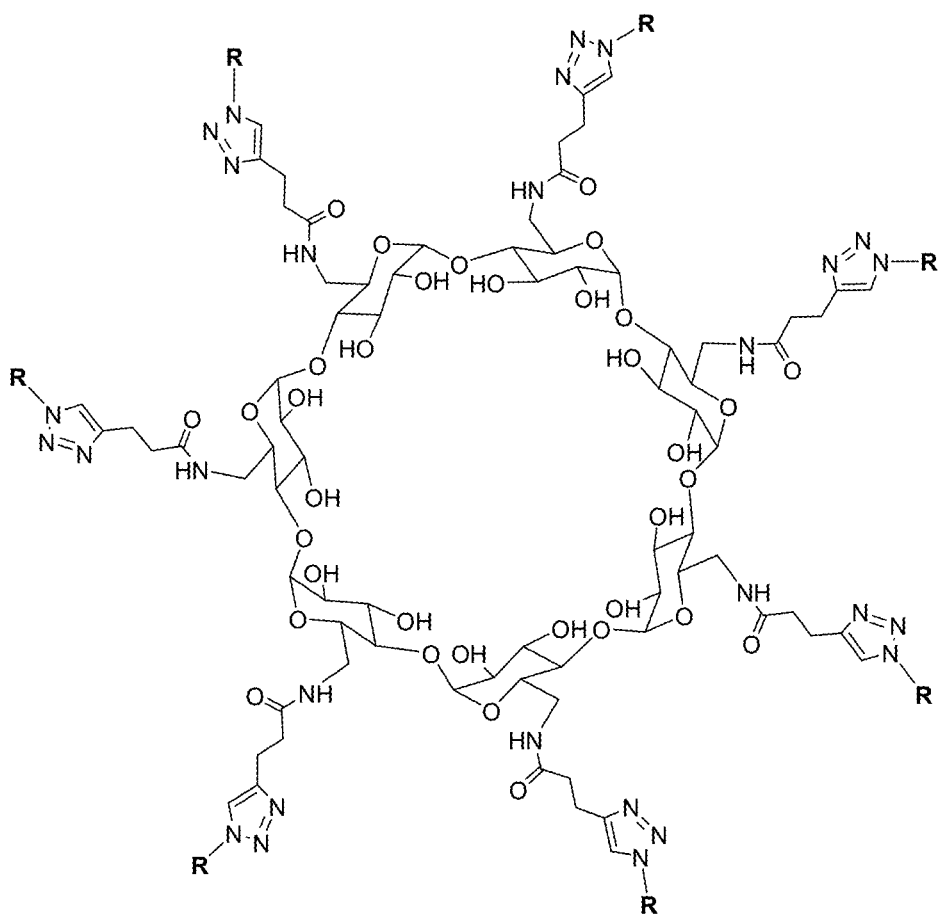

In some embodiments, the galectin 3 inhibitor may be Multivalent Inhibitor C of FIG. 4, or a pharmaceutically acceptable salt thereof.

In some embodiments, the galectin 3 inhibitors described herein are configured to self-assemble to form micelles in vitro or in vivo under physiological conditions.

In some embodiments, the galectin 3 inhibitors described herein are selective galectin 3 inhibitors. In some embodiments, the galectin 3 inhibitors are inhibitors of both galectin 3 and galectin 1.

In some embodiments, the galectin 3 inhibitors described herein amphiphilic.

In some embodiments, the galectin 3 inhibitors described herein are assembled to form micelles in vitro and such micelles are delivered according to the methods and compositions described herein as galectin 3 inhibitors.

In some embodiments, the invention includes galectin 3 inhibitor micelles having a plurality of compounds of formula I, formula II, and/or formula III, as described herein.

Pharmaceutical Compositions

In one embodiment, the invention provides a pharmaceutical composition for use in the treatment of the diseases and conditions described herein. In a preferred embodiment, the invention provides pharmaceutical compositions, including those described below, for use in the treatment of sepsis and/or septic shock. In an embodiment, the invention includes a pharmaceutical composition for use in the treatment of sepsis and/or septic shock that includes one or more galectin 3 inhibitors as described herein.

In some embodiments, the concentration of the galectin 3 inhibitor provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the galectin 3 inhibitor provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the galectin 3 inhibitor provided in the pharmaceutical compositions is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the galectin 3 inhibitor provided in the pharmaceutical compositions is independently in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the galectin 3 inhibitor provided in the pharmaceutical compositions is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the galectin 3 inhibitor provided in the pharmaceutical compositions is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The galectin 3 inhibitors according to the invention are effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

In a preferred embodiment, the pharmaceutical compositions of the present invention are for use in the treatment of sepsis and/or septic shock that results from pneumococcal pneumonia.

Described below are non-limiting pharmaceutical compositions and methods for preparing the same.

Pharmaceutical Compositions for Oral Administration

In preferred embodiments, the invention provides a pharmaceutical composition for oral administration containing a galectin 3 inhibitor, or a pharmaceutically acceptable salt thereof, and a pharmaceutical excipient suitable for administration.

In some embodiments, the invention provides a solid pharmaceutical composition for oral administration containing: (i) an effective amount of a galectin 3 inhibitor, and (ii) a pharmaceutical excipient suitable for administration.

In some embodiments, the invention provides a solid pharmaceutical composition for intranasal and/or oral aerosol administration containing: (i) an effective amount of a galectin 3 inhibitor, and (ii) a pharmaceutical excipient suitable for administration.

In some embodiments, the pharmaceutical composition may be a liquid pharmaceutical composition suitable for oral administration.

In some embodiments, the pharmaceutical composition may be a liquid pharmaceutical composition suitable for intranasal and/or oral aerosol administration.

Pharmaceutical compositions of the invention suitable for oral administration can be presented as discrete dosage forms, such as capsules, sachets, tablets, liquids, or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

The galectin 3 inhibitors as active ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques. For example, in the preparation of dry dosage forms for inhalation, the solid galectin 3 inhibitor, or pharmaceutically acceptable salt thereof, may be provided on a solid carrier, such as a lactose carrier.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, 6-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In some embodiments, the invention provides a pharmaceutical composition for injection containing a galectin 3 inhibitor, or a pharmaceutically acceptable salt thereof, and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating a galectin 3 inhibitor, or a pharmaceutically acceptable salt thereof, in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of a galectin 3 inhibitor, or a pharmaceutically acceptable salt thereof, or pharmaceutical composition of such compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), via local delivery by catheter or through inhalation.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a galectin 3 inhibitor, or a pharmaceutically acceptable salt thereof, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In some embodiments, the galectin 3 inhibitor, or a pharmaceutically acceptable salt thereof, and another active pharmaceutical ingredient are provided as separate compositions in separate containers within the kit. In some embodiments, the galectin 3 inhibitor, or a pharmaceutically acceptable salt thereof, and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

In some embodiments, the kits of the invention may include one or more of a dry powder inhaler, an aerosol inhaler, and a nebulizer, depending upon whether the galectin 3 inhibitor provided therewith is provided as a solid dosage form or liquid dosage form.

In some embodiments, the invention provides a kit comprising a composition comprising a therapeutically effective amount of a galectin 3 inhibitor, or a pharmaceutically acceptable salt thereof. These compositions are typically pharmaceutical compositions.

The kits described above are preferably for use in the treatment of the diseases and conditions described herein. In a preferred embodiment, the kits are for use in the treatment of sepsis and/or septic shock.

Dosages and Dosing Regimens

The amounts of a galectin 3 inhibitor, or a pharmaceutically acceptable salt thereof, administered will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of a galectin 3 inhibitor, or a pharmaceutically acceptable salt thereof, may be provided in units of mg/kg of body mass or in mg/m² of body surface area.

In some embodiments, the galectin 3 inhibitor, or a pharmaceutically acceptable salt thereof, is administered in a single dose. Such administration may be by injection, e.g., intravenous injection, in order to introduce the galectin 3 inhibitor, or a pharmaceutically acceptable salt thereof, quickly. However, other routes, including the preferred oral or intranasal route, may be used as appropriate. A single dose of a galectin 3 inhibitor, or a pharmaceutically acceptable salt thereof, may also be used for treatment of an acute condition.

In some embodiments, a galectin 3 inhibitor, or a pharmaceutically acceptable salt thereof, is administered in multiple doses. In an embodiment, a galectin 3 inhibitor, or a pharmaceutically acceptable salt thereof, is administered in multiple doses. Dosing may be once, twice, three times, four times, five times, six times, or more than six times per day. Dosing may be once a month, once every two weeks, once a week, or once every other day. In other embodiments, a galectin 3 inhibitor, or a pharmaceutically acceptable salt thereof, is administered about once per day to about 6 times per day. In some embodiments, a galectin 3 inhibitor, or a pharmaceutically acceptable salt thereof, is administered once daily, while in other embodiments, a galectin 3 inhibitor, or a pharmaceutically acceptable salt thereof, is administered twice daily, and in other embodiments a galectin 3 inhibitor, or a pharmaceutically acceptable salt thereof, is administered three times daily.

Administration of the active pharmaceutical ingredients of the invention may continue as long as necessary. In some embodiments, a galectin 3 inhibitor, or a pharmaceutically acceptable salt thereof, is administered for more than 1, 2, 3, 4, 5, 6, 7, 14, or 28 days. In some embodiments, a galectin 3 inhibitor, or a pharmaceutically acceptable salt thereof, is administered for less than 28, 14, 7, 6, 5, 4, 3, 2, or 1 day. In some embodiments, a galectin 3 inhibitor, or a pharmaceutically acceptable salt thereof, is administered chronically on an ongoing basis—e.g., for the treatment of chronic effects. In another embodiment the administration of a galectin 3 inhibitor, or a pharmaceutically acceptable salt thereof, continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of a galectin 3 inhibitor disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a galectin 3 inhibitor disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of a galectin 3 inhibitor disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a galectin 3 inhibitor disclosed herein is about 0.01 mg/kg to about 0.35 mg/kg, or to about 0.7 mg/kg, or to about 1 mg/kg, or to about 1.4 mg/kg, or to about 1.8 mg/kg, or to about 2.1 mg/kg, or to about 2.5 mg/kg, or to about 2.85 mg/kg, or to about 3.2 mg/kg, or to about 3.6 mg/kg.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of a galectin 3 inhibitor, or a pharmaceutically acceptable salt thereof, may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, or as an inhalant.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Design and Synthesis of Galectin Inhibitors

Figure 8:
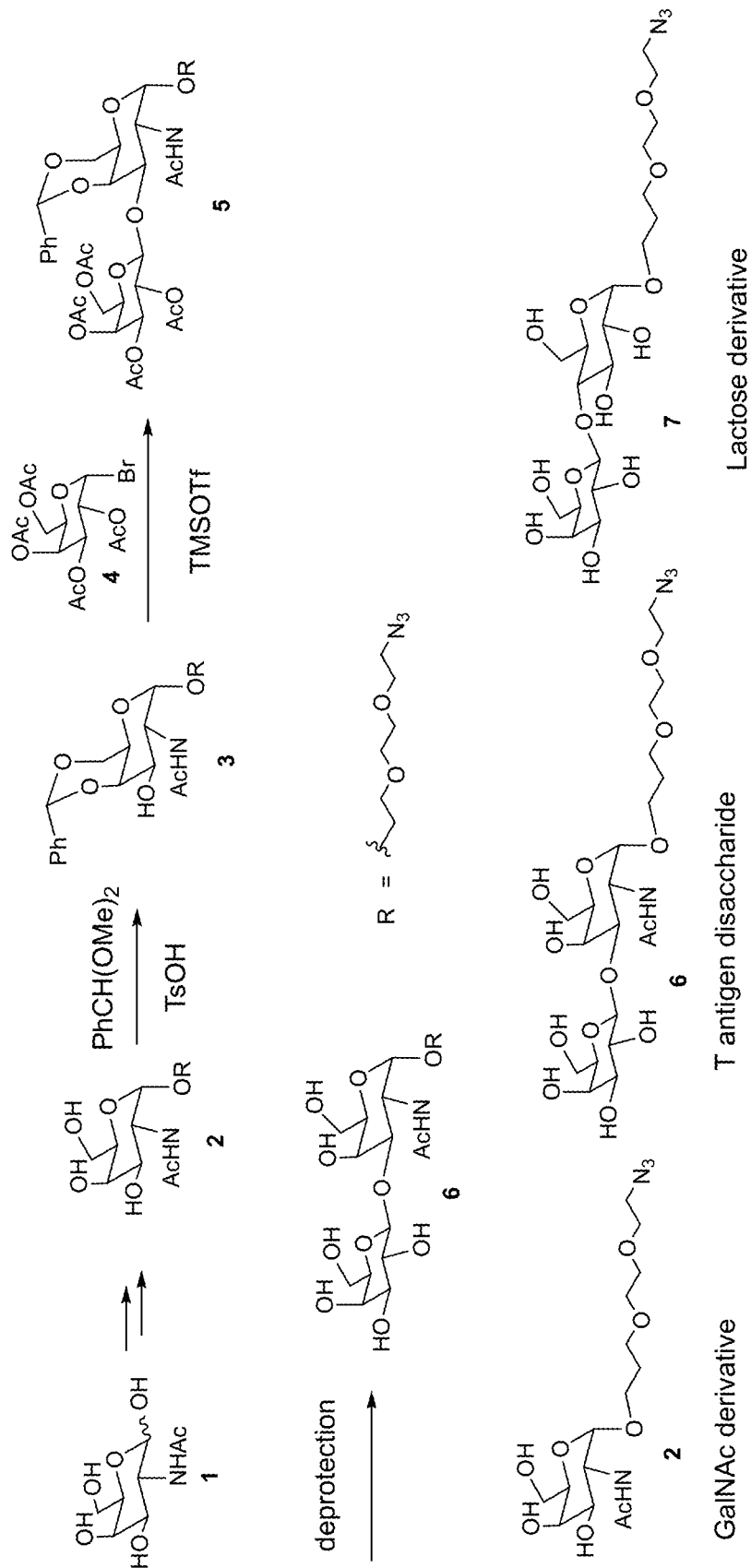
FIG. 8 illustrates an exemplary chemical synthesis of the disaccharide building blocks for making multivalent galectin ligands.

Both Gal1 and Gal3 recognize galactose-terminated glycoconjugates but they show ligand selectivity and the binding affinity depends on the context of the glycoconjugate structures. Previous studies have shown that lactose or N-acetyllactosamine terminal structures are preferred substrates for galectin 1, while galectin 3 has much higher affinity for the Thomsen-Friedenreich (Tf) antigen which possesses a Galβ1,3GalNAc disaccharide moiety. In addition, multivalency is important for high affinity interactions with galectins. Multivalent inhibitors for galectin 1 and galectin 3 are provided herein using cyclodextrin (CD) as a platform. Commercially available cyclodextrins are cyclic oligosaccharides consisting 6-8 glucose units linked in α-1, 4-glycosidic linkages (named α-, β-, and γ-cyclodextrins, respectively). CDs have been used as a template for multivalent glyco-ligand design as the hydroxyl groups at the two rims can be subjected to selective introduction of functionality. The synthesis of the present designed CD-based galectin inhibitors is summarized in FIGS. 8 to 10.

For example, the Tf antigen disaccharide subunit and a lactose derivative will be synthesized using N-acetylgalactosamine, galactose, or lactose, as starting materials.

Figure 9:
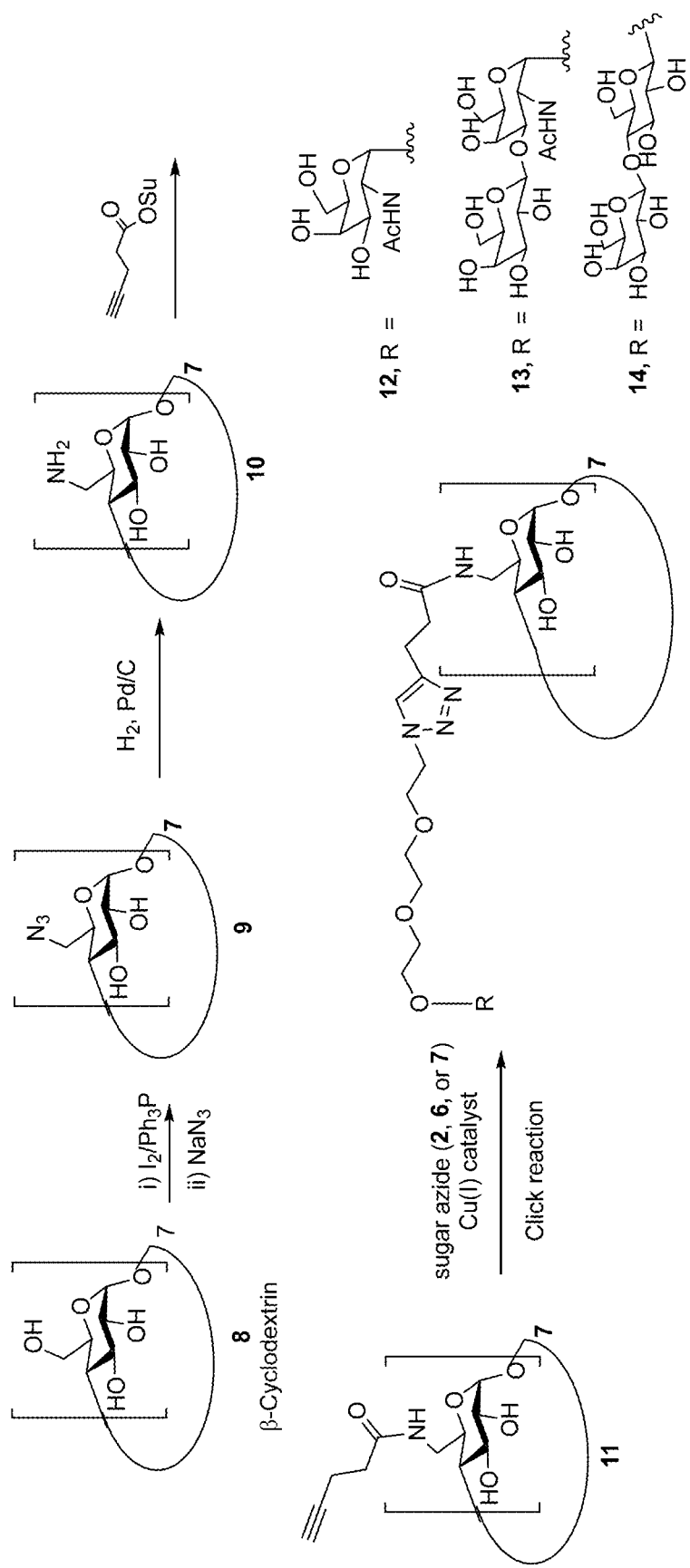
FIG. 9 illustrates an exemplary synthesis of cyclodextrin-based multivalent galectin ligands.

Well-established chemical glycosylation methods will be applied for the synthesis of the mono- and disaccharide ligands as building blocks (compounds 2, 6, and 7). The aglycon part is functionalized with an azide group, which is ready for click reaction for conjugation to an alkyne-functionalized cyclodextrin template for the assembling of the multivalent (FIG. 8). β-cyclodexin (β-CD) will be selected as a template for multivalent display of the disaccharide ligands. (β-CD will be first functionalized at the primary hydroxyl rim to introduce the azide groups, which are then converted into amino groups by hydrogenation. Then, the amino groups are functionalized with the alkyne functionality. Click reaction between the alkyne and the azido group in the mono- and disaccharide building blocks (compounds 2, 6, and 7) yields the multivalent inhibitors (compounds 12, 13, and 14, respectively) (FIG. 9).

Figure 10:
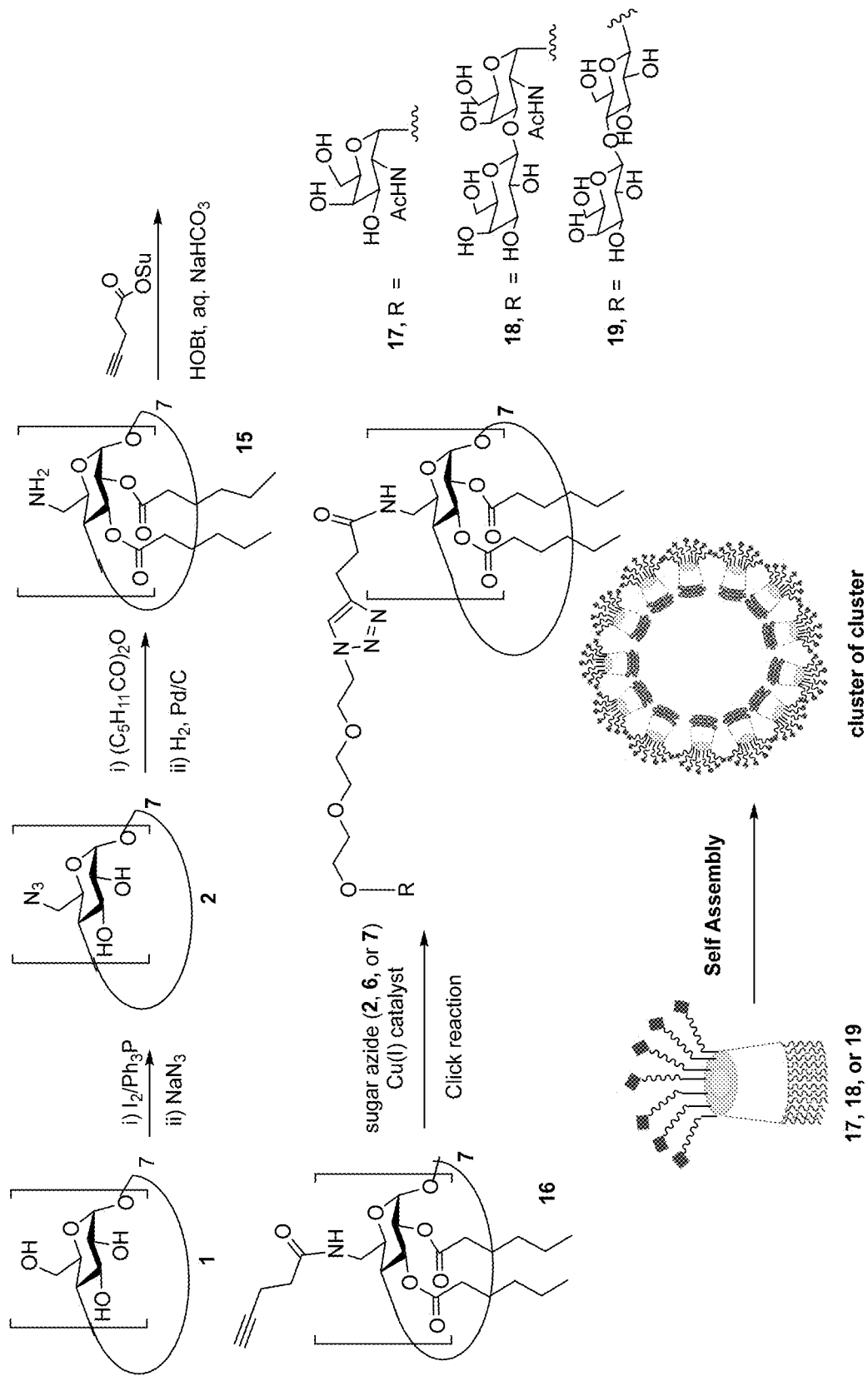
FIG. 10 illustrates an exemplary synthesis of cyclodextrin-based multivalent galectin ligands in which lipid moieties are introduced at the rim of the secondary hydroxyl groups for self-assembly.

As another design, to make novel self-assembling multivalent inhibitors, a lipid group is introduced at the secondary hydroxyl rim before reduction of the azide group in the CD derivative. Then, the alkyne group is introduced by reduction and acylation to give the alkyne derivative (16). Finally, click reaction between the alkyne 16 and the azide group in the mono- and disaccharide building blocks (compounds 2, 6, and 7) yields the multivalent inhibitors (compounds 17, 18, and 19, respectively) (FIG. 10).

Without being limited to any one theory of the invention, it is expected that compounds 12, 13, 14, 17, 18, and 19 will have much higher affinity to galectin 3 and galectin 1, respectively, than the disaccharide subunits themselves, due to the multivalent display. Moreover, a particularly innovative aspect of this design is that the introduction of the lipid chains on the other rim would make the inhibitors amphiphilic, which will allow them to form micelles under physiological conditions, adding another level of multivalency to further enhance the inhibitory activity (FIG. 10). This hypothesis will be tested by both in vitro and in vivo experiments.

Figure 11:
FIG. 11 illustrates exemplary bi-antennary, tri-antennary, and tetra-antennary N-Glycan precursors that may be linked to cyclodextrins as described herein.
Figure 11:
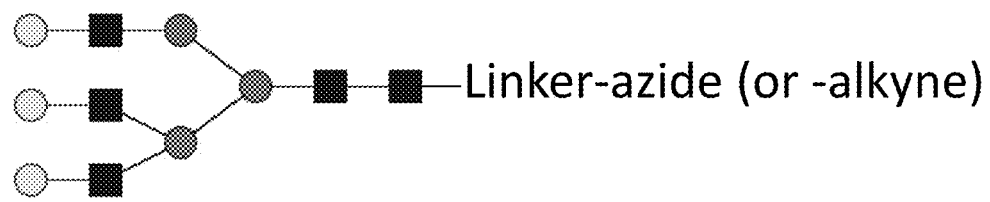
Figure 11:
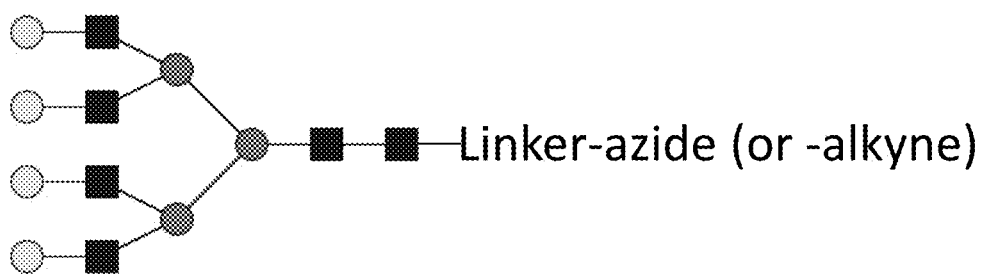

Furthermore, exemplary bi-antennary, tri-antennary, and tetra-antennary N-glycan moieties that may be connected to the cyclodextrins provided herein are shown in FIG. 11, which may be connected through click chemistry as described above.

Both monovalent and CD-based multivalent inhibitors were synthesized, with non-reducing terminal galactosyl moieties, namely lactose (Lac), N-acetylgalactosamine (GalNAc), and the Thompsen-Friedenreich disaccharide (TFD; Galβ1,3GalNAc).

Synthesis of TFD with azide linker is depicted in Scheme 1A. Chemical synthesis of TFD with azide linker poses a degree of complexity in comparison with modified lactose. To produce the functionalized TFD, a strategy for efficient synthesis of TFD, which had Tn (GalNAc) antigen as a key intermediate, was used.

Scheme 1A
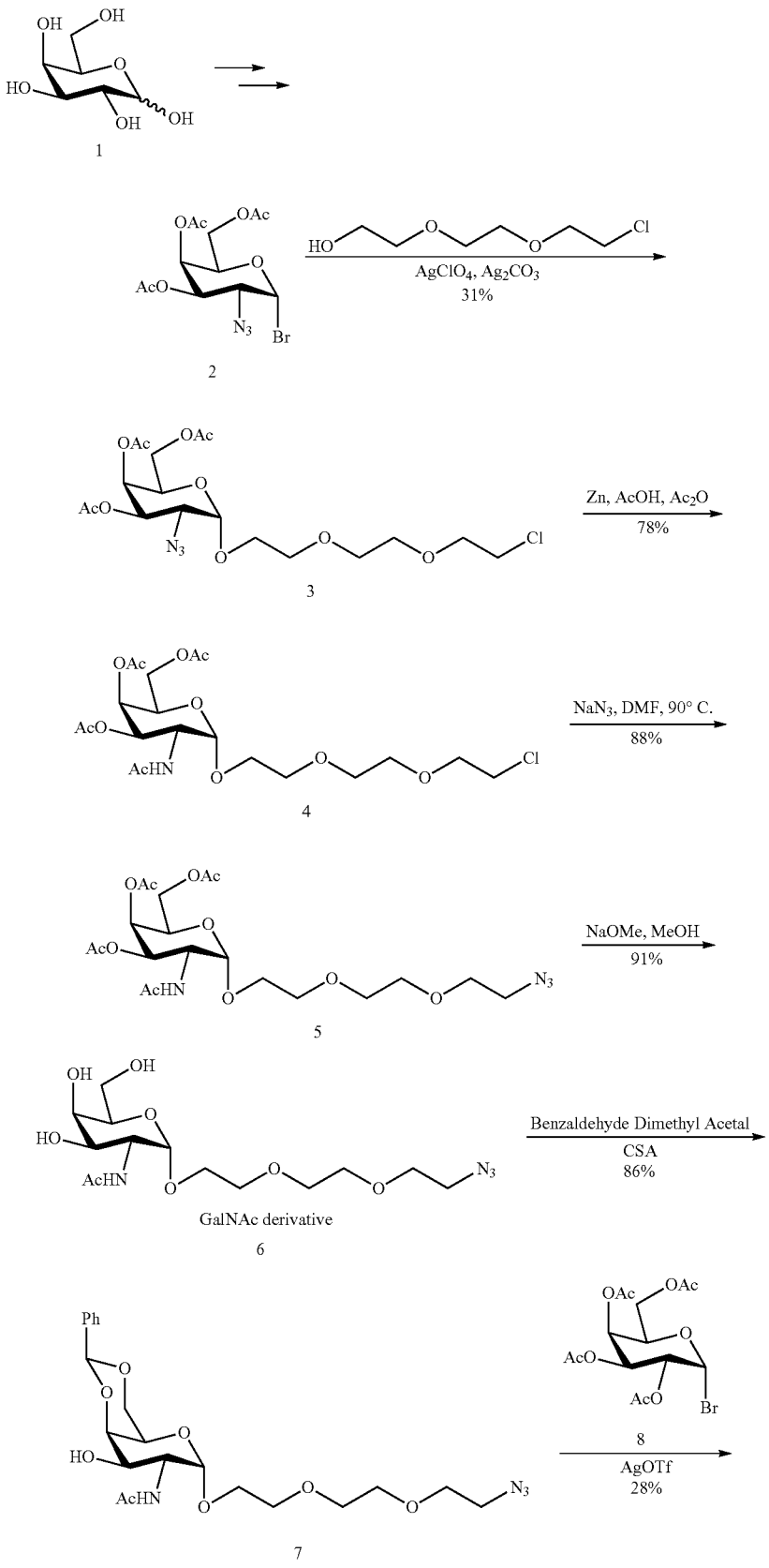

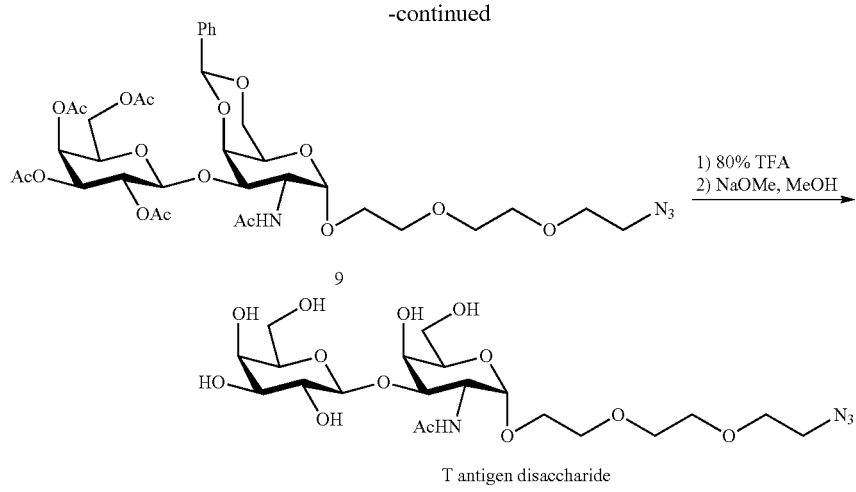

T antigen disaccharide
10

The synthesis of CD-based multivalent Gal3 inhibitors requires the mono and disaccharide ligands, which are "clicked" on the modified CD scaffold. The synthesis started with the glycosylation between the glycosyl donor (2) and the PEG linker, with modified Koenigs-Knorr's method under catalysis of $AgClO_4$ and $Ag_2CO_3$ to provide the alpha isomer (3), in which 2-azido group is to avoid neighboring group participation by N-acetyl group at the C-2 (Scheme 1A). The compound with α-galactoside linkage for the newly generated glycosidic bond was purified by chromatography and was determined by its relatively small coupling constants (3.2 Hz) between the H-1 and H-2 of the α-galactoside. There was no selectivity between α- and β-form (nearly 1:1 molar ratio). Reduction of the 2-azido to the 2-acetamido group was achieved by treatment of 3 with Zinc, acetic acid, and acetic anhydride to provide monosaccharide derivative (4). Then the chloride on the terminal of the PEG was substituted by azide to give the O-acetyl protected GalNAc derivative (5). Global deprotection of the O—Ac groups via catalytic hydrogenolysis with NaOMe in MeOH gave the free GalNAc derivative (6) in quantitative yield (91%). To synthesize the TF antigen disaccharide, 5 was selectively protected on C-4 and C-6 hydroxyl groups by benzaldehyde dimethyl acetal catalyzed by CSA to yield the monosaccharide (7). The GalNAc derivative (19) was glycosylated with the glycosyl donor (8) under the catalysis of AgOTf to give the disaccharide (9). The O-acetyl group at the C-2 of the glycosyl donor ensures the formation of the β-glycosidic linkage for the newly formed glycosidic bonds via neighboring group participation. Deprotection of the O-Bn groups in 80% TFA, followed by NaOMe in MeOH gave the free TFD derivative (10). After purification, the identity of the product was confirmed by MS and NMR ($^1H$ and $^{13}C$) analysis.

Synthesis of the lactose derivative is depicted in Scheme 1B.

Scheme 1B

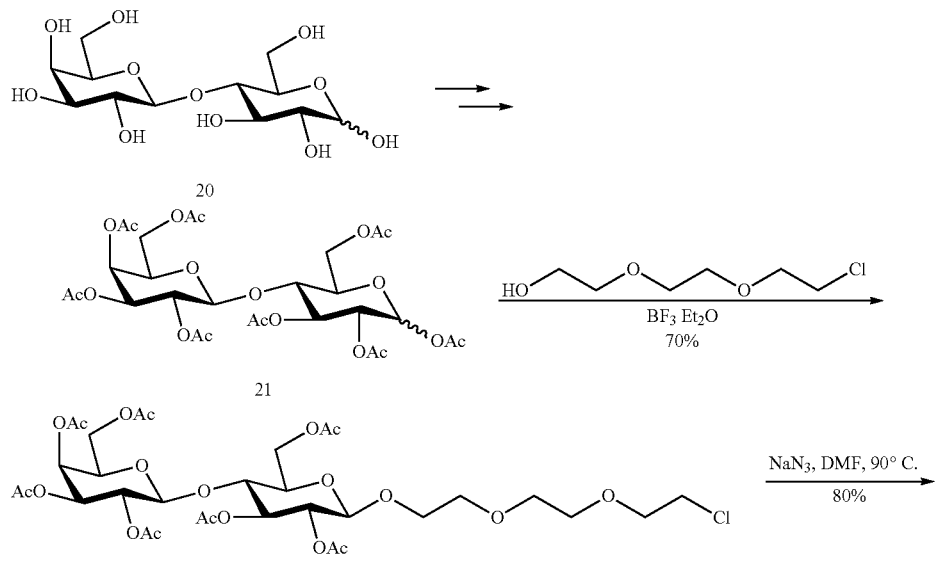

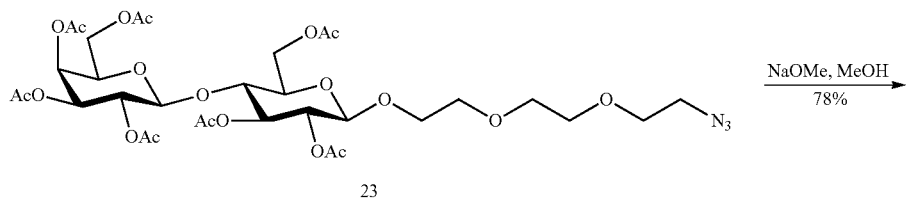

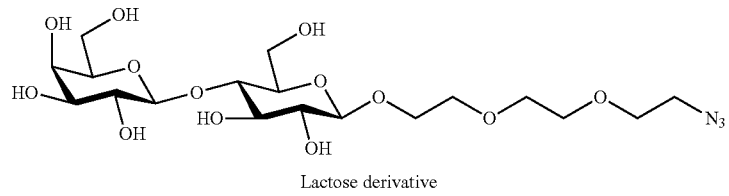

The disaccharide (21) was glycosylated with the PEG glycosyl donor under the catalysis of BF$_3$.Et$_2$O to give the tetrasaccharide (22). The O-acetyl group at the C-2 of the glycosyl donor ensures the formation of the α-glycosidic linkage for the newly formed glycosidic bonds via neighboring group participation. Conversion of the chloride group into azido group was achieved by treatment of 22 with NaN$_3$ at 90° C. to afford the intermediate (23). Then global deprotection of 25 by catalytic hydrogenolysis provided free lactose azide derivative (26), which was characterized by MS and NMR ($^1$H and $^{13}$C) analysis.

Synthesis of functionalized β-cyclodextrin is depicted in Scheme 2. To synthesize functionalized β-cyclodextrin (Scheme 2), selective conversion of the C-6 hydroxyl groups to the iodo groups was first performed, followed by reaction with NaN$_3$ to give the per-6-azido derivatives β-CD (13), following the previously reported procedure.

Scheme 2

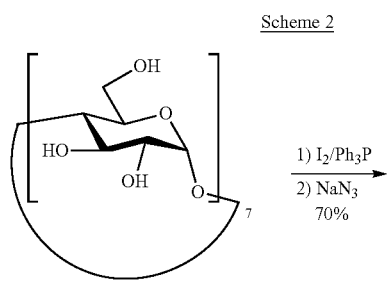

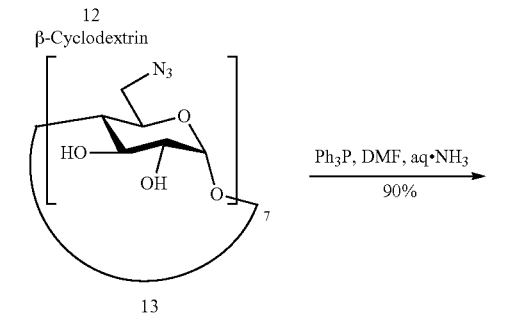

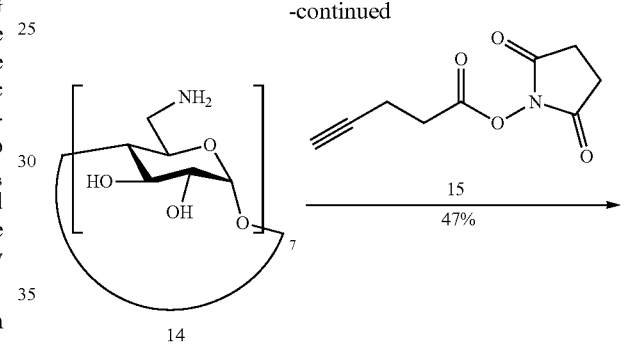

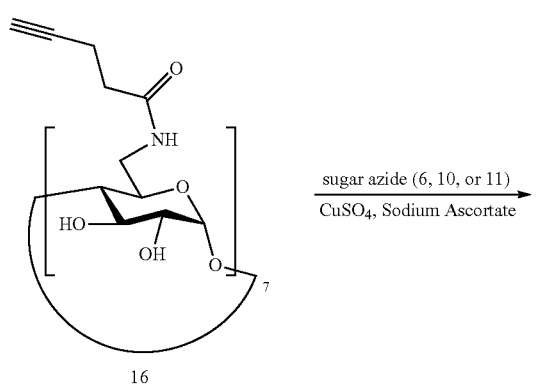

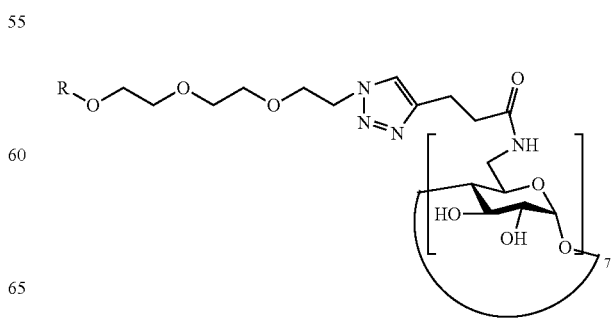

-continued

17 R = 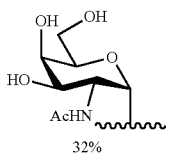
32%

18 R = 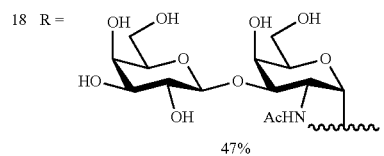
47%

19 R = 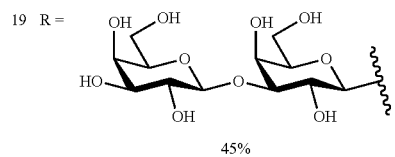
45%

Reduction of 6-azido group into 6-amino group was achieved by treatment of 13 with Ph$_3$P to afford the key intermediate (14). To introduce the alkyne groups, amine coupling reaction between 14 and activated 4-Pentynoic acid (15) was first performed at pH 8.5, followed by gel filtration purification. The result was confirmed by MS and NMR analysis.

The conjugation between the three sugar azides (6, 10, and 11) with the per-6-alkyne derivatives of β-CD (16) is also shown in Scheme 2. Compound 6 was first reacted with the per-6-azide-β-CD using 1.5:1 ratio of azide:alkyne in an aqueous solution. The desired conjugate 17 was isolated in 32% yield after gel filtration purification. In a similar fashion, the conjugation of TF antigen disaccharide 10 and lactose derivatives with 16 was also successful, providing the desired conjugates (18 and 19) in 47% and 45% yield. The identities of all final glycoconjugates were confirmed by NMR ($^1$H and $^{13}$C) in D$_2$O and high-resolution mass spectrometry.

Example 2—Galectins Regulate the Inflammatory Response in Airway Epithelial Cells by Modulating the Expression of SOCS1 and RIG1

In this study, it is demonstrated in vitro that the combined activity of microbial neuraminidases and the secreted Gal1 and Gal3 at the epithelial cell surface modulate the expression of SOCS1 and RIG1 and activation of ERK, AKT or JAK/STAT1 signaling pathways, leading to a disregulated expression and release of pro-inflammatory cytokines.

Reagents

Phenylmethanesulfonyl fluoride (PMSF), trypsin, and bacterial neuraminidases α (2⇒3,6,8,9) *Arthrobacter ureafaciens, Clostridium perfringens* were purchased from Sigma (St. Louis, Mo.), or QA-bio (Palm Desert, Calif.), respectively. Antibodies against, NF-kappaB p65 and phospho-NF-kappaB p65 (Ser 311) were obtained from Santa Cruz Biotechnology (Santa Cruz, Calif.). Antibodies against integrin β3, phospho-integrin 133, ERK, phospho-ERK, AKT, phospho-AKT, p38 MAPK, phospho-p38 MAPK, STAT1 and phospho-STAT1 were purchased from Sigma (Saint Louis, Mo.). Protease inhibitor cocktail set I, β-mercaptoethanol, and 100× penicillin/streptomycin were obtained from Calbiochem (La Jolla, Calif.). Dialysis tubing (MW:6-8000) was purchased from Spectrum Laboratories (Rancho Dominguez, Calif.). TRIzol Reagent was obtained from Invitrogen (Camarillo, Calif.). Dulbecco's modified Eagle's medium (DMEM) was purchased from Cellgro (Manassas, Va.). Prestained broad range protein marker was obtained from Cell Signaling Technology (Danvers, Mass.). PD Mini Trap G10 was purchased from GE Healthcare (Pittsburgh, Pa.). Mini Protean TGX precast gels, phosphate buffered saline (PBS), resolving buffer, and stacking buffer were all purchased from Bio-Rad (Hercules, Calif.). One minute western blot stripping buffer was obtained from GM Biosciences (Frederick, Md.). Polyvinylidene fluoride (PVDF) membrane was purchased from Millipore Thermo Scientific (Rockford, Ill.). Western Lightning Plus-ECL was purchased from PerkinElmer Inc (Waltham, Mass.). Molecular biology grade agarose was purchased from Denville Scientific Inc (Metuchen, N.J.). Dream Taq PCR master mix (2×) and Revertaid first strand cDNA synthesis kit was purchased from Thermo Scientific (Pittsburgh, Pa.), Fetal bovine serum (FBS) was obtained from Quality Biological Inc (Gaithersburg, Md.). Oligonucleotide primers for RT-PCR were synthesized by Sigma-Aldrich, Human proinflamatory 9-Plex ultra-sensitive kit and human IL-15 ultra-sensitive kit were purchased from Meso Scale Discovery (Gaithersburg, Md.).

Expression and Purification of Recombinant Human Galectin-1 (rhGal1) and Human galectin-3 (rhGal3)

Expression of rhGal1 and rhGal3 were performed using the pT7 (ML-1) and pET30 Ek/Lic vectors in the *Escherichia coli* BL21 (DE3) (Novagen; Billerica, Mass.) cells and induced by 0.1 mM isopropyl D-thiogalactoside (Sigma-Alderich) at 23° C. for 16 h in 3 liters of LB medium containing 100 μg/ml amphicilin and 30 μg/ml kanamycin. The soluble proteins extracted with Bugbuster (Novagen) containing 1 mM PMSF and 0.07% β-mercaptoethanol (2-ME), contained most of the recombinant proteins: rhGal1 and rhGal3 (approximately 80%). These fractions were loaded onto a column packed with 4 ml of lactose-Sepharose. After washing the column thoroughly with 0.07% 2-ME in 1:10 PBS [PBS (1:10)/2-ME] for rhGal1 and 0.07% 2-ME in PBS (1×) for rhGal3, the rhGal1 was eluted with 0.1M lactose in PBS (1:10)/2-ME and rhGal3 with 0.1M lactose in PBS (1×). From a 3-liter *E. coli* culture, approximately 17 mg of rhGal1 and 30 mg of rhGal3 were purified. Carbamidomethylation of rhGal1 was performed as previously reported (Feng et al. 2013). Purified rhGal1 (17 mg) was absorbed on a 1 ml of DEAE-Sepharose pre-equilibrated with PBS (1:10)/2-ME, and incubated for 1 h at 4° C. with slow agitation. The resin was poured into a column and after extensive washing with PBS (1:10), the column was overlaid with 3 ml of 0.1M iododacetamide/0.1 M lactose and incubated for 1 h at 4° C. in the dark. After washing the column with 50 mM lactose in PBS (1:10), the bound protein (crhGal1) was eluted with PBS (1:10)/0.5 M NaCl/ 0.1M lactose.

Airway Epithelial Cell Primary Cultures and Cell Line

A549 cells (human alveolar type II epithelial cell line derived from a lung adenocarcinoma; ATCC: CCL-185, Manassas, Va.) were cultured in DMEM containing 10% FBS supplemented with 50 units/ml penicillin and 50 μg/ml streptomycin as previously described (Lillehoj et al. 2012).

RT-PCR

Total RNA from cultured A549 cells was extracted with TRIzol Reagent. RNA was quantified in a Nanodrop Bio-analyzer at 260/280 nm. Complementary DNA (cDNA) was synthesized using Revertaid first cDNA synthesis kit from 1 μg of total RNA according to the manufacturer's instructions. cDNAs were amplified using Dream Taq PCR Master Mix (2×) and the following primers: human SOCS1, forward, 5'-TTTTCGCCCTTAGCGTGAA-3' (SEQ ID NO: 1); reverse, 5'-GCGGCGCGGCGCCGCCACG-3' (SEQ ID NO: 2); human RIG1, forward, 5'-ACCAGACCTCCTCTTGGC-3' (SEQ ID NO: 3); reverse, 5'-GAAGGGGCAGATGGCTGT-3' (SEQ ID NO: 4); human δ-actin, forward, 5'-CCGCGCTCGTCGTCGACAAC-3' (SEQ ID NO: 5); reverse, 5'-GCTCTGGGCCTCGTCGCCC-3' (SEQ ID NO: 6). The PCR products were fractionated on 1% agarose gels and visualized by ethidium bromide staining.

Real-time PCR

Total RNA from cultured A549 cells was extracted and cDNA was synthesized as described above. cDNA transcribed from 10 ng of total RNA was amplified at 7500 Fast Real-Time PCR System (Applied Biosystems) using Fast SYBR Green Master Mix according to the manufacture's recommendation and the following primers: human SOCS1, forward, 5'-GACGCCTGCGGATTCTACTG-3' (SEQ ID NO: 7); reverse, 5'-CACGCTAAGGGCGAAAAAGC-3' (SEQ ID NO: 8); human RPS13 5'-CGAAAGCATCTTGAGAGGAACA-3' (SEQ ID NO: 9); reverse, 5'-TCGAGCCAAACGGTGAATC-3' (SEQ ID NO: 10). The relative gene expression of SOCS1 was calculated using the ΔCt method, and normalized to the reference gene, PRS13, as an internal control (Cross et al. 2012).

Enzyme Treatments

Cultured A549 cells were subject to neuraminidase treatment (300 mU of neuraminidase per $1 \times 10^6$ cells in 200 µl) at 37° C. for 1 h in serum-free DMEM. After incubation, the cells were washed three times in PBS and resuspended in DMEM without FBS for detection of galectins and cytokines.

Western Blot

Cells were lysed with ice cold 50 mM Tris-HCl, pH 7.4, 150 mM NaCl, 1% (v/v) Triton X, protease inhibitor, 0.1 mM PMSF. The cell lysates were assayed for protein concentration at 280 nm using Nanodrop Bioanalyzer. Equal amounts of protein were resolved by electrophoresis on commercial gradient SDS-polyacrylamide gels and transferred to PVDF membrane. The membranes were blocked in 5% nonfat milk and then probed with primary antibodies at 1:1000 dilutions. Next, membranes were washed in PBS-T followed by incubation with HRP-linked secondary antibody (1:3000) and the results were visualized with Western Lightning Plus-ECL reagents.

Expression of SOCS1 and RIG1, and Secretion of Cytokines in A549 Cells Exposed to Neuraminidase and Galectins A549 cells grown on 6 well plates were treated with NeuK (combination of *A. ureafaciens* and *C. perfringens* neuraminidases, 300 mU per $1 \times 10^6$ cells in 200 µl) at 37° C. for 1 h. After the treatment, cells were washed three times with PBS then incubated in FBS-free DMEM with rhGal1 or rhGal3 (15 µg/ml, final concentration) for 1 h. Cells were collected and total RNA obtained was used for detection of SOCS1 and RIG1 transcripts. The culture medium was collected and added to plated pre-coated with cytokine-specific antibodies for assessment of cytokine levels using an MSD human proinflamatory 9-Plex Assay Ultra-Sensitive Kit to measure IFN-γ, TNF-α, IL-113, IL-6, IL-8, IL-10 and IL-12, and MSD human IL-15 Assay Ultra-Sensitive Kit to determine levels of IL-15, following MSD manufacturer's instructions.

Statistical Analyses

The protein or RT-PCR amplicon bands were quantified using Image J software. Comparison of two groups was performed by Student's t-test for the comparison of non-paired samples. All results with p<0.05 were considered statistically significant.

Results and Discussion

It has been reported that the expression and secretion of galectins, particularly galectin-1 (Gal1) and galectin-3 (Gal3), are modulated during IAV infection, and that their levels in the bronchoalveolar space remain high upon recovery from influenza (Nita-Lazar et al. 2015a). This observation led to testing in an in vitro system whether microbial neuraminidases and galectins could contribute to the dysregulation of the lung immune response with the ensuing cytokine storm. In a prior study (Nita-Lazar et al. 2015a), the expression of galectins and their secretion to the extracellular environment were examined in primary small airway epithelial cells (SAEC) and the airway epithelial cell line A549 cells. Moreover, the viral neuraminidase unmasks galactosyl moieties in the airway epithelia, which promotes binding of the abovementioned galectins and contributes to enhance pneumococcal adhesion by cross-linking the bacteria to the cell surface. Like in the lung tissues, both the SAEC and the A549 cells express galectins 1 and 3, and secrete them to the extracellular space. Thus, a suitable in vitro model was considered to further characterize the potential role(s) of microbial sialidases and host galectins in the regulation of the immune response to influenza and a subsequent pneumococcal infection, with a particular focus on their effects on the expression of SOCS and cytokine expression and secretion profiles.

Figure 5:
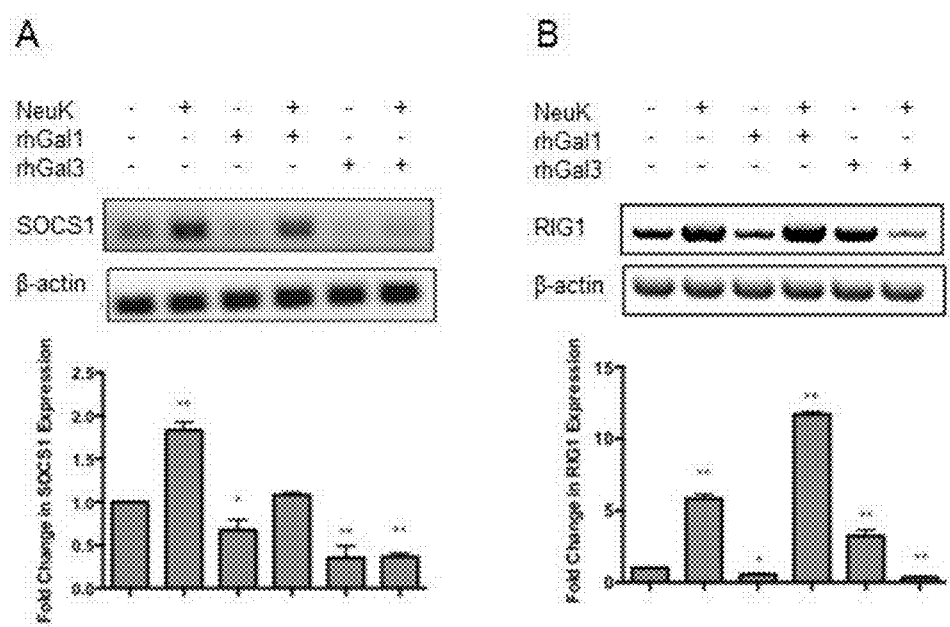

Expression of SOCS and RIG1 in Epithelial Lung Carcinoma Cells (A549) Exposed to Microbial Neuraminidase and Galectins:

First, real-time PCR was examined to determine the potential variability of SOCS1 expression in A549 cells during the culture period for which the experiments were designed. The results revealed that SOCS1 expression levels in A549 cells remained constant over the 4-day growth period, under standard culture conditions. Next, the potential effects of microbial neuraminidase treatment and exposure to extracellular Gal1 and Gal3 on the expression of SOCS1 and RIG1 was examined. Activity of the exogenous neuraminidase (combination of *A. ureafaciens* and *C. perfringens* neuraminidases: NeuK) on the A549 cells increased SOCS1 expression levels in about 2-fold (FIG. 5). Exposure of untreated cells to rhGal1, significantly decreased SOCS1 expression in 20-30%, but when the cells had been pretreated with NeuK, the SOCS1 expression returned to the control levels. Exposure of the untreated or NeuK-treated A549 cells to rhGal3, however, downregulated SOCS1 expression in about 60-70% of the control levels.

Exposure of the airway epithelial cells to microbial neuraminidase and galectins had opposite effects on SOCS1 expression. While the microbial neuraminidase significantly increased SOCS1 expression levels (consistent with the increased pro-inflammatory cytokine expression), the subsequent exposure to Gal1 compensated this effect, retracting SOCS1 expression to the control levels, suggesting that Gal1 would have a homeostatic effect that would enable a controlled inflammatory response aimed at clearing the potential threat. The regulatory roles of Gal1 in immune homeostasis have been well established (Camby et al. 2006; Rabinovich and Ilarregui 2009). Gal1 displays anti-inflammatory activity (Rabinovich et al. 1999; Santucci et al. 2003; Toscano et al. 2006), mediates apoptosis of activated T-cells in peripheral tissues (Koh et al. 2008), and exerts ant proliferative effects on epithelial tumor cell lines by inhibition of the Raps-ME-ERK pathway (Fischer et al. 2005).

Figure 6:
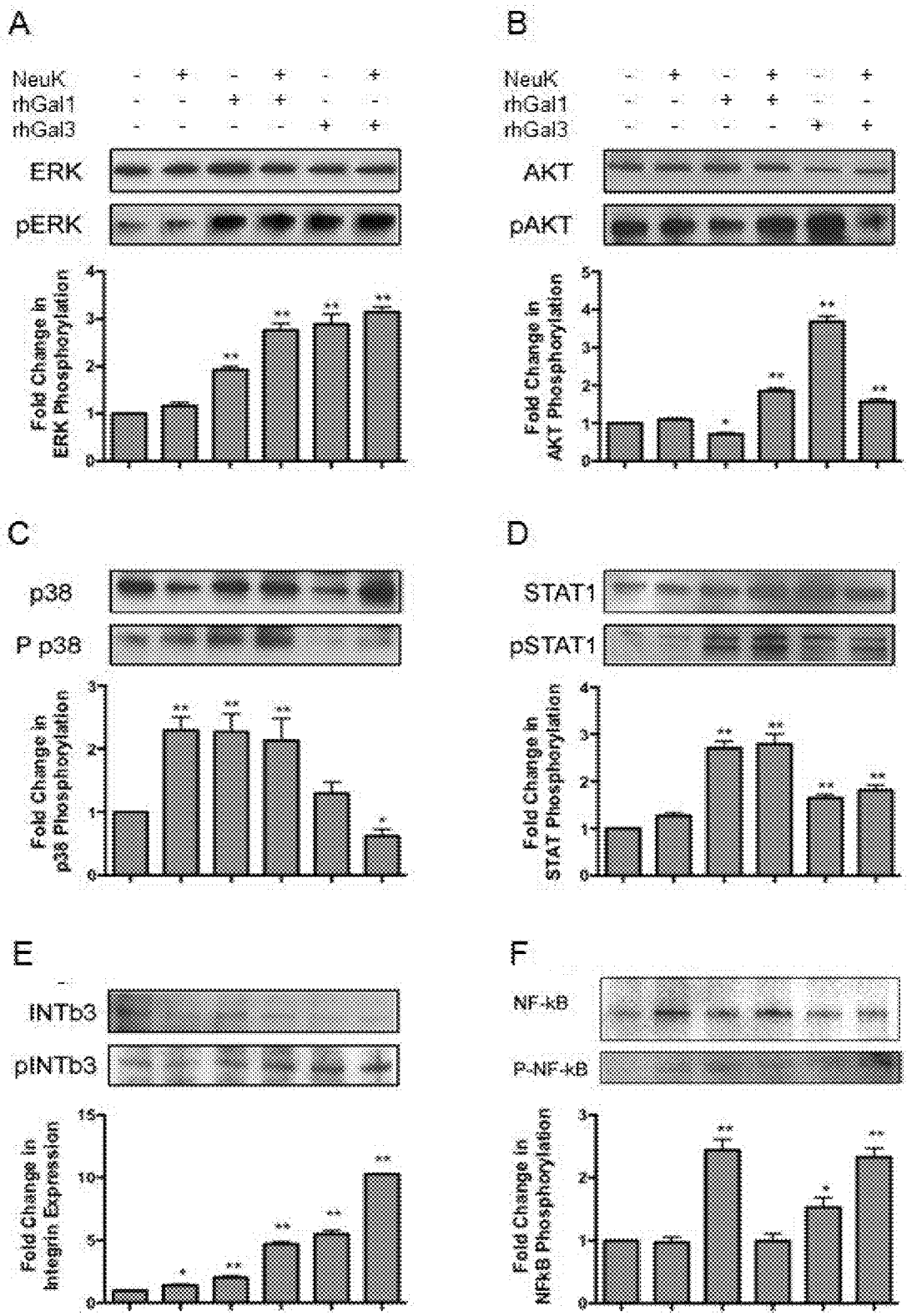

The anti-inflammatory activity of Gal11 takes place through the inhibition of IκB-α degradation that is induced by pro-inflammatory stimuli, the increase of cytoplasmic retention of p65, and a decrease of DNA binding activity of NF-κB, that attenuates NF-κB activation and impairs the transcriptional activation of immune genes (Toscano et al. 2011). Our results indicate that at the same time, Gal1 downregulates SOCS1 expression. In both the unexposed and neuraminidase-exposed cells, the extracellular Gal3 also had an effect opposite to the upregulatory effect of neuraminidase on SOCS1 expression, since it significantly decreased the SOCS1 transcript levels. Like we observed for Gal1, downregulation of SOCS1 expression by Gal3 would enable the robust cytokine response directed to induce the effective anti-microbial response. This is consistent with the protective role of Gal3 reported for pneumococcal infection in a murine model (Sato et al. 2002). In experimental pneumococcal infections in the mouse, Gal3 functions as a soluble adhesion molecule to mediate the integrin-independent recruitment of neutrophils to *S. pneumonia*-infected lungs (Sato et al. 2002). Furthermore, in contrast with the anti-inflammatory activity of Gal1, Gal3 displays pro-inflammatory activity. For example, Gal3 can directly activate neutrophils, augment neutrophil phagocytosis of bacteria, delay neutrophil apoptosis, facilitate phagocytosis of apoptotic neutrophils by macrophages, and exert bacteriostatic in vitro activity against *S. pneumoniae* (Farnworth et al. 2008). These results revealed that upon a prior influenza infection, the high levels of Gal1 and Gal3 remaining in the bronchoalveolar space during the recovery period are further increased immediately after a pneumococcal challenge (Nita-Lazar et al. 2015). Thus, the synergistic effect of increased Gal3 levels in the extracellular space together with the availability of additional galactosyl moieties on the epithelial cell surface resulting from the influenza neuraminidase, would downregulate SOCS1 expression far below the unexposed control levels, leading to an uncontrolled hypercytokinemia (Pothlichet et al. 2008). SOCS1, a JAK binding protein, belongs to the SOCS family that is responsible for key negative feedback mechanisms to prevent uncontrolled inflammation (Croker et al. 2008). Upon IAV challenge, SOCS1 expression is upregulated through a RIG1/MAVS/IFNAR1-dependent pathway (Pothlichet et al. 2008), which suppresses expression of inflammatory cytokines, e.g. IL-6, TNF-α, IL-10, CCL3, CCL5, CCL4 and CXCL8, to prevent the cytokine storm (Ramirez-Martinez et al. 2013). Thus, upregulation of SOCS1 provides a negative feedback mechanism to set inflammation under control after pathogen clearance. In this context, the galectin-mediated downregulation of SOCS1 expression would upset this balance, leading to a cytokine storm, especially on tissues exposed to the viral neuraminidases. It is possible that exposure of the epithelial cell surface to the pneumococcal neuraminidase would synergistically enhance this effect upon the pneumococcal challenge (Nita-Lazar et al. 2015b).

Expression of RIG1 was significantly increased by NeuK treatment alone (6-fold) whereas exposure to rhGal1 alone decreased RIG1 expression to about 50% of the unexposed control (FIG. 5). Exposure of NeuK-pretreated A549 cells to rhGal1 increased RIG1 expression in about 12-fold. The effects of rhGal3 on RIG1 expression were opposite to rhGal1: exposure to rhGal3 alone upregulated RIG1 expression in about 4-fold, whereas the NeuK treatment followed by exposure to rhGal3 downregulated RIG1 expression to about 20% of the unexposed controls. RIG1 is a member of the RIG-I-like receptor family, and functions as a pattern recognition receptor (PRR) and sensor for viruses such as influenza A, Sendai virus, and flavivirus (Yoneyama and Fujita 2009; Yoo et al. 2014). In addition to all-trans retinoic acid (ATRA), LPS (TLR4-mediated), type I interferon, and other agonists up-regulate RIG1 expression (Matsumiya and Stafforini 2010). RIG1 activates two distinct downstream TRAF-mediated signaling pathways: the IRF3/7 and NFkB pathways (Matsumiya and Stafforini 2010). Together with SOCS1, upregulation of mRNA levels of RIG1 in IAV infection suppresses expression of inflammatory cytokines, and thus prevents hypercytokinemia (Ramirez-Martinez et al. 2013). Furthermore, upon IAV infection the upregulation of RIG1 induces upregulation of SOCS1 expression (Pothlichet et al. 2008), and our results on the effects of neuraminidases and galectins on epithelial cells are consistent with the association of RIG1 and SOCS1 expression.

The exposure of epithelial cells to extracellular Gal1 or Gal3 had opposite effects on RIG1 expression, and either exacerbated or reversed dramatically the effects of prior exposure to microbial neuraminidase. Gal1 alone downregulated the expression of RIG1, whereas if the cells had been pretreated with neuraminidase, the effect on RIG1 expression was dramatically reversed. In contrast, the presence of extracellular Gal3 alone significantly upregulated RIG1, while it had the opposite effect on the neuraminidase exposed cells. The results strongly suggest that cleavage of terminal sialic acids by the microbial neuraminidase exposed on the cell surface additional or novel galactosyl moieties that could activate different signaling pathways leading to either upregulation or downregulation of RIG1, and in turn, of SOCS1. While a cytokine-mediated signaling pathway can upregulate SOCS1 expression, viral infection can also do so through various mechanisms. For example, upon IAV infection SOCS1 expression is mediated by RIG1 (Pothlichet et al. 2008), but if the cells are exposed to the nonstructural protein (NS1) of the respiratory syncytial virus (RSV), SOCS1 is upregulated in a RIG1- or TLR3-independent manner (Xu et al. 2014). Therefore, it becomes clear that the associated expression of RIG1 and SOCS1 depends on the external stimuli, and in this context, the extracellular Gal1 and Gal3 may play different roles depending of the prior exposure of the cells to viral or bacterial neuraminidase.

Activation of Signaling Pathways in A549 Cells Exposed to Neuraminidase and Galectins:

Based on the modulation of SOCS and RIG1 expression by the synergic activities of microbial neuraminidase and galectins, we examined the possible signaling pathways that may be activated in the process. Phosphorylation levels of integrin 33 (INTβ3), ERK, AKT, p38 MAPK, STAT1 and NF-κB were assessed by western blot in untreated (control; Ctrl) or NeuK-treated A549 cells either in the presence or absence of 15 μg/ml rhGal1 or rhGal3 (FIG. 6). The phosphorylation level of p38, a MAPK component, increased 2.5-fold in NeuK-treated A549 cells, but ERK, AKT and STAT1, as a JAK/STAT pathway, remained unchanged. The treatment of A549 cells with exogenous rhGal1 increased the phosphorylation levels of ERK, p38 and STAT1 between 2- and 3-fold, but decreased AKT to 50% of the control level. The NeuK treatment of A549 changed the effect of exogenous rhGal1 on AKT, increasing it up to 2-fold. The other proteins, ERK and STAT1, were also increased, but p38 remained at the level of the NeuK-treated A549 control. Exogenous rhGal3 induced an opposite effect for AKT phosphorylation than rhGal1 in A549 cells, as AKT phosphorylation increased up to 4-fold (FIG. 6). The phosphorylation levels induced by exogenous rhGal3 in A549 also increased for ERK and STAT1, but remained unchanged for p38. The NeuK treatment of A549 cells changed the effect of exogenous rhGal3 for p38 (decreasing the phosphorylation more than 50%) compared with rhGal3 effect on untreated cells. rhGal3 induced a 3-fold increase for ERK, 1.5-fold for AKT and up to 2-fold for STAT1. The phosphorylation of NF-κB was enhanced by addition of rhGal1 (up to 3-fold) or rhGal3 (up to 2-fold). The NeuK treatment of A549 cells alone did not modify the NF-κB phosphorylation level, but the further exposure to rhGal3 enhanced phosphorylation of NF-κB up to 3-fold (FIG. 6).

The modulation of SOCS and RIG1 expression by the synergic activities of microbial neuraminidase and galectins at the airway cell surface, suggested that selected signaling pathways may be activated in the process leading to regulatory effects on expression and release of pro- and anti-inflammatory cytokines and chemokines. Our results revealed that the exposure of the epithelial cells to microbial neuraminidase and Gal1 or Gal3 led to the selective activation of different key regulatory signaling pathways. The activity of the microbial neuraminidase on the surface of A549 cells only activated the p38 MAPK signaling pathway, and enhanced INT33 phosphorylation, while all other pathways examined showed no phosphorylation changes in their selected components tested. This finding is not only consistent with the observation that infection by IAV inhibits expression of type I IFN and IL-6 by increasing SOCS expression via p38 MAPK activation (Bode et al. 2001; Pauli et al. 2008), but further suggests that the activity of influenza neuraminidase on the airway epithelial cell surface may be responsible for inducing the anti-inflammatory response resulting from enhancing SOCS expression via RIG1 and p38 MAPK activation. It is noteworthy that type I IFN display a pro-inflammatory role by activating NK cells (Nguyen et al. 2002), but it can also exert anti-inflammatory activity by inhibiting IL1, IL18 and IL12, or by enhancing IL10 production (Billiau 2006; Guarda et al. 2011; Gonzalez-Navajas et al. 2012; Arimori et al. 2013). In this regard, our study showed that the exposure of A549 cells to Gal1 maintained the MAPK activation levels, but significantly increased the phosphorylation levels of ERK, p38, STAT1 and NF-κB, while if the cells were previously exposed to neuraminidase the phosphorylation levels were increased further. Exposure of A549 cells to exogenous NeuK greatly increases INTβ3 phosphorylation. Further, desialylation increases LPS-mediated TLR4 activation (Feng et al. 2012), and 132 integrin interacts with TLR4 and modulate the NF-κB and MAPK activation (Perera et al. 2001; Yee and Hamerman 2013). Because INTβ3 may serve as coreceptor of TLR2 and boost the TLR2 signaling in response to viral or bacterial stimuli (Gianni et al. 2012; Gianni and Campadelli-Fiume 2014), its activation/phosphorylation could facilitate the interaction with TLR and modulate the downstream signaling or mediate the NF-κB activation directly. Effects of the exposure of the untreated cells to Gal3 were opposite to neuraminidase since except for p38, all components tested were significantly phosphorylated, particularly ERK and AKT. However, if the cells had been previously exposed to neuraminidase, exposure to Gal3 reduced p38 phosphorylation below the control levels, while phosphorylation of AKT was reduced to half, while phosphorylation levels of INTβ3 and NF-κB were maximally increased. The effect of Gal3 towards activation of AKT was opposite to that observed for Gal1.

Figure 7:
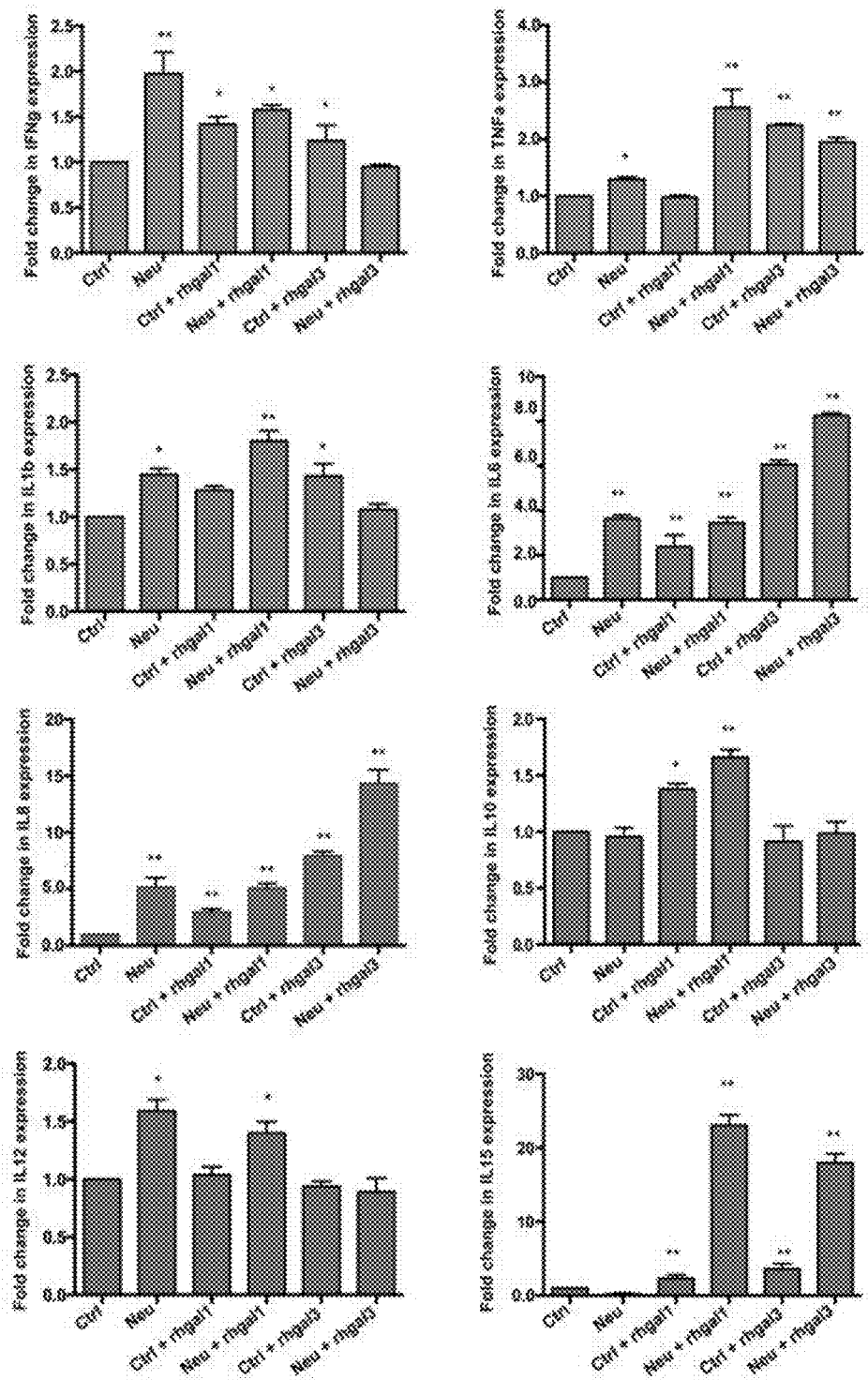

Cytokine Secretion from A549 Cells Exposed to Microbial Neuraminidase and Galectins:

Finally, the potential impact of the downregulation of SOCS and RIG1 was examined by the combination of microbial neuraminidases and galectins on the expression and secretion of cytokines. For this, the cytokine released to the supernatant by the galectin and NeuK-treated cells was quantitatively assessed. Treatment of the cells with microbial neuraminidase alone enhanced to various degrees the extracellular levels of most cytokines tested [interferon-γ (IFNγ); tumor necrosis factor-α (TNFα); interleukin-1β (IL-1β); IL-6; IL-8; and IL-12] whereas IL-10 and IL-15 remained unchanged as compared to the untreated A549 cells (FIG. 7). When the untreated A549 cells were exposed to 15 μg/ml of exogenous rhGal1 the levels of IFNγ, IL-6, IL-8, and IL-10 increased, while TNFα, IL-1β, and IL-12 remained unaffected. Gal3 exposure (15 μg/ml) increased levels of IFNγ, TNFα, IL-10, IL-6, and IL-8, whereas levels of IL-10 and IL-12 were unchanged. Pre-exposure of the A549 cells to NeuK further enhanced the rhGal1-mediated upregulation of all cytokines tested, particularly noticeable for the pro-inflammatory cytokines IL-6 (4-fold) and IL-15 (25-fold) and the chemokine IL-8 (5-fold). Similarly to rhGal3, the NeuK treatment of the A549 cells further upregulated most cytokine and chemokine levels in the culture supernatant, with most significant increases for IL-6 (8-fold), IL-8 (15-fold), and IL-15 (20-fold), but had no effect on IL-1β, IL-10 and IL-12.

The exposure of A549 cells that had been subjected to prior neuraminidase exposure to exogenous Gal1 reversed the anti-inflammatory response of neuraminidase toward a pro-inflammatory response by moderately downregulating SOCS expression to reach the control levels. This is supported by the observation that in addition to enhancing the release of pro-inflammatory cytokines such as IFNγ, TNFα, and IL-6, and the chemokine IL-8, exposure of the cells to extracellular Gal1 also increased the release of the anti-inflammatory cytokine IL-10, suggesting a balance between pro- and anti-inflammatory activities. This would take place by the activation of the ERK and AKT pathways, which involved in type I IFN production that in turn, induce pro-inflammatory responses by activating the JAK/STAT pathway. As a result, a controlled antimicrobial innate immune response aimed at clearing the microbial challenge would be fully enabled. The binding of Gal3 to the airway epithelial surface exposed to viral and bacterial neuraminidase, however, dramatically downregulates the expression of SOCS1 and RIG1 in neuraminidase-exposed epithelial cells further enhancing the pro-inflammatory responses resulting from the Gal1-mediated mechanism described above. The maximal levels of NF-κB phosphorylation levels observed in cells exposed to both neuraminidase and Gal3 suggest that expression and release of pro-inflammatory cytokines are significantly enhanced. Consistent with this observation are the increases of all pro-inflammatory cytokines and chemokines tested, whereas release of IL-10 remained unchanged. Proinflammatory cytokine signaling at the cell surface induces expression of SOCS proteins through the STAT1 pathway. In turn, the upregulated SOCS inhibit the JAK/STAT signaling, which negatively affects the downstream expression of many inflammatory cytokines, thereby providing a feedback loop to prevent the overwhelming inflammatory responses. More specifically, SOCS1 blocks p38, c-Jun N-terminal kinase (JNK), and nuclear factor κB (NF-κB) activation, and downregulates the expression of transforming growth factor-β-activated kinase 1 (TAK1) (Choi et al. 2013). Our results revealed that exogenous Gal3 downregulated expression of SOCS1 expression most likely through the p38 pathway, whose phosphorylation was significantly inhibited by Gal3. Among the multiple layers of negative feedback regulation, the p38

MAPK pathway plays a central role to many of the feedback loops to prevent unprovoked, excessive, or unduly prolonged expression of pro-inflammatory genes (Clark and Dean 2012). For example, p38 MAPK upregulates expression of SOCS3, which negatively regulates IL-6 expression (Ehlting et al. 2007; Kiu et al. 2007). Therefore, inhibition of the p38 MAPK pathway signaling by Gal3, would ultimately lead to an uncontrolled upregulation of the expression of inflammatory cytokines.

Conclusions

These results suggest that the activity of the viral and pneumococcal neuraminidase on the surface of the airway epithelial cells function as a "danger signal" that alerts the system and rapidly induces expression of SOCS to prevent an uncontrolled inflammatory response, which is "fine-tuned" by the presence of galectins in the extracellular space and their binding to galactosyl moieties unmasked on the surface of airway epithelial cells. Thus, the high levels of Gal1 in the bronchoalveolar space during the influenza infection and recovery counteract the effect of the viral neuraminidase on the airway epithelium, and enables an effective response of both pro-(IFNγ, TNFα, IL-6, IL-8) and anti-inflammatory cytokines and chemokines that "fine-tunes" the inflammatory response and the controlled clearance of the viral infection. During the recovery from influenza infection, however, the levels of Gal3 in the bronchoalveolar space increase dramatically as early as 1 h upon the pneumococcal challenge, and as a consequence, the expression of SOCS1 via RIG1 and p38 MAPK is further downregulated, multiple proinflammatory pathways are activated, particularly ERK and JAK/STAT, and NF-κB is maximally phosphorylated. This results in significant increases in the expression and release of pro-inflammatory cytokines whereas the anti-inflammatory cytokines, such as IL-10 remain unaffected. As a consequence, the pro- and anti-inflammatory cytokine balance would be grossly tilted towards an exaggerated response leading to a hypercytokinemia and septic shock.

Example 3—In Vivo Testing of Galectin 3 Inhibitors in Murine Sepsis Model

A murine study may be prepared as described herein to examine the effect of galectin 3 inhibitors in a model for a human clinical scenario, which provides for post-influenza secondary pneumococcal superinfection and ensuing sepsis. In this model, the mice that recovered from a sub-lethal dose of influenza A virus (IAV) challenge are more susceptible to pneumococcal challenge than the naïve mice (Chen et al., 2012). In the experimental IAV/pneumococcal pneumonia/sepsis model, at day 1 the mice (C57BL/6J, 6-8 week-old) are anesthetized with isoflurane (Baxter; Deerfield, Ill.) prior to the deposition of 10-20 µl of challenge inoculum to a single nare. The inoculum is prepared 1 h prior to challenge from frozen stocks of the mouse-adapted IAV/PuertoRico/08/1934 strain (PR8) which is diluted to the desired sublethal challenge concentration, in sterile, endotoxin-free PBS (Biosource International, Rockville, Md.). The mice are allowed to recover from the flu, and at day 14 the animals are anesthetized again and sub-lethally infected with the deposition of 10-20 µl of challenge pneumococcal inoculum [*Streptococcus pneumoniae* serotype III (Sp3); ATTC; Manassas, Va.)] to a single nare.

As a result, the animals develop an uncontrolled, fatal pulmonary pneumococcal infection and cytokine dysregulation (sepsis). Studies show: (a) the expression and secretion of galectin-3 (Gal3) is modulated during IAV infection, (b) that the IAV neuraminidase unmasks galactosyl moieties in the airway epithelia, and (c) that the binding of secreted Gal3 to the airway epithelial cell surface downregulates the expression of SOCS, leading to a disregulated expression and release of pro-inflammatory cytokines, and sepsis (Nita-Lazar et al Mol. Immunol, 2015a,b).

Administration of synthetic high affinity multivalent cyclodextrin-TFD based inhibitors (mvCD-TFD) for Gal3, as described herein, via the respiratory tract (ie. aerosol inhaler, nebulizer, dry powder) upon influenza and prior to (or during) pneumococcal pneumonia can be used to (1) prevent the binding of the Gal3 present in the bronchoalveolar space to the epithelial surface, (2) prevent the downregulation of expression of SOCS, and (3) prevent/ameliorate sepsis.

To prevent or ameliorate sepsis by the use of mvCD-TFD in the aforementioned experimental mouse model, at days 12 and 13 after the PR8 challenge (see challenge protocol above) the mice are nebulized (Aeroneb® Lab Micropump Aerosol Nebulizer, Kent Scientific Co.; Torrington, Conn.) every 12 hours with the mvCD-TFD in liquid vehicle formulation. At day 14 the mice are experimentally infected with Sp3, as described above, and nebulized every 12 hours with the mvCD-TFD Gal3 inhibitor as described above. From days 15 to 18 the mice are nebulized once a day.

Figure 12:
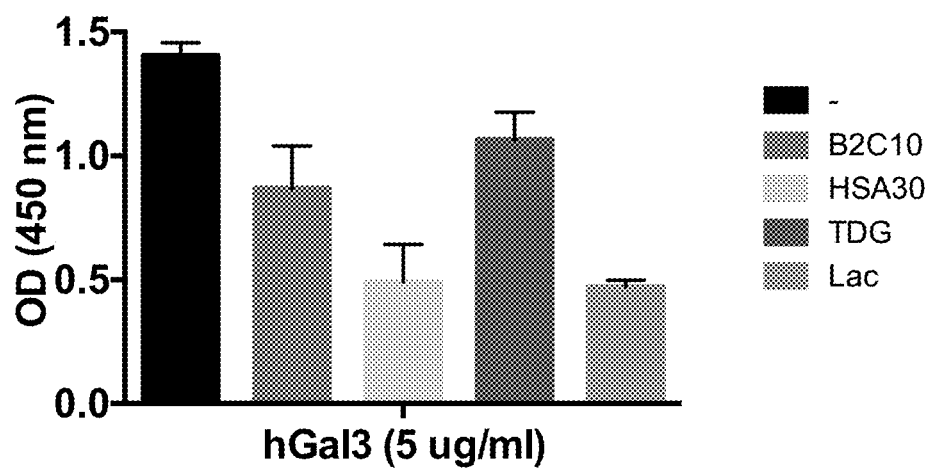
FIG. 12 illustrates that both an antibody and a synthesized glycoconjugate partially inhibit the galectin binding, along with the disaccharide TDG and lactose.

Example 4—Inhibition of hGal3 Binding to Asialofetuin by Various Inhibitors and an Anti-Gal3 Antibody Ninety-six well microtiter plates were coated with 1 ug/well of asialofetuin (10 µg/ml in PBS, 100 ul each well) for 3 h at 37° C., washed and blocked with 3% BSA in PBS overnight at 4° C. After washing, biotinylated recombinant human Gal3 (rhGal3, 5 ug/ml, 100 ul) was pre-mixed with inhibitors (-, PBS only; B2C10, anti-Gal3 antibody (B2C10); HSA30, HAS-Gal$_{30}$ (Wang H et al., Bioorganic & Medicinal Chemistry, Vol 21, Issue 7, P2037-44); TDG, thiodigalactoside 5 mM; Lac, lactose 50 mM) before adding onto each well, and incubated at 4° C. for 1 h. The binding was revealed by incubation with streptavidin-conjugated horseradish peroxidase (HRP) followed by TMB substrate. The reaction was stopped with 1 M HCl and the optical density (OD) at 450 nm from each well was measured by SpectraMax 340 plate reader (Molecular Device). Data show the mean OD and standard error in each condition from triplicate wells. Both antibody and synthesized glycoconjugate partially inhibit the galectin binding, along with the disaccharide TDG and lactose (FIG. 12).

Example 5—Binding of rhGal3 to A549 Cells and Inhibition by Natural and Synthetic Inhibitors, and Antibodies Against MUC1 and β1integrin Partially Inhibit Gal3 Binding onto A549 Cells A549 cells were trypsinized for single cell suspension and fixed for the flow cytometry analysis. One million cells were incubated in 100 ul of PBS with 0 to 10 µg/ml (as indicated) of biotinylated hGal3 for 1 h at 4° C., followed by 1 h of incubation with FITC-conjugated streptavidin. After washing, the cell suspension was analyzed in C6 cytometer. Data show the mean fluorescent intensity (MFI) with SE of each sample (FIG. 13A). Dose-dependent binding onto A549 cells was observed (FIG. 13B). The A549 cells were incubated with hGal3 in 10 g/ml pre-mixed with 50 mM of lactose (Lac 50 mM), 50 mM (TDG 50) or 10 mM of thiodigalactoside (TDG 10), and analyzed as above. Cells incubated with buffer only was included as background control (bkg). Both Lac and TDG inhibit binding well. Similar results from hGal3 in 3 µg/ml (data not shown). Both disaccharides inhibit the binding of rhGal3 onto A549 cells. For inhibition studies, the A549 cells were incubated with hGal3 in 10 µg/ml pre-mixed with 0~10 mM of TDG (data not shown) or TF disaccharides (right panel), and analyzed as above. Cells incubated with buffer only was included as background control (bkg). Both disaccharides inhibit the binding.

Antibodies against MUC1 and β1integrin partially inhibit Gal3 binding onto A549 cells. The A549 cells were pre-incubated with anti-MUC1 and -β1integrin antibodies for 30 min, followed by addition of rhGal3 (10 ug/ml), and analyzed as above. Both antibodies partially inhibit rhGal3 binding (FIG. 13C), which without wishing to be bound by any particular theory, suggests that the cell surface ligands for Gal3 binding are not limited to β1integrin and MUC1, and other receptors are involved.

Example 6—Monovalent Vs Multivalent Inhibitors of Gal3 Binding

A549 cells were incubated with rhGal3 pre-mixed different concentration of multivalent TFD, Lac, or GalNAc. The mean fluorescent intensity (MFI) of each sample with inhibitors was compared with A standard curve with different concentration of Gal3 vs mean fluorescent intensity (MFI) without inhibitor to interpolated the "relative concentration", which was used to calculated the percentage inhibition (%) as (original concentration-relative concentration)/original concentration×100. All three compounds inhibit the binding in dose-dependent manner, disaccharides (TFD and Lac) are better than GalNAc, and TFD has better inhibition capacity at the lower concentrations (FIG. 14A). To compare the inhibitory efficiency of mono- and multivalent inhibitors A549 cells were incubated with Gal3 pre-mixed with different concentration of monovalent (GalNAc Mono) or multivalent compounds of N-Acetylgalactosamine (GalNAc Multi; FIG. 14B). Multivalent compound inhibits the binding better than monovalent. Without wishing to be bound by any particular theory, it is suggested that in some embodiments, multivalency is a factor in inhibitory capacity of the synthetic compounds.

Based on these results, a comparative inhibition study was carried out and the IC50 of multivalent and monovalent compounds calculated (FIG. 15). A549 cells were cultured in 96-well plates, fixed, and incubated with biotinylated rhGal3 (5 ug/ml) pre-mixed with different concentration of monovalent or multivalent compounds (mvCD) for 1 h at 4° C. The binding was revealed by incubation with streptavidin-conjugated horseradish peroxidase (HRP) followed by TMB substrate as described herein. The OD of each sample with inhibitors was compared with a standard curve with different concentration of Gal3 vs OD to interpolated the "relative concentration", which was used to calculated the % inhibition as (original concentration-relative concentration)/original concentration×100; FIG. 15A). The % inhibition with different inhibitors was further drawn over concentration of inhibitors to calculate their IC50, using GraphPad Prism's non-linear fit function and interpolating the concentration to achieve 50% inhibition (FIG. 15B).

Example 7—Downregulation of SOCS Expression by Gal3, and Inhibition of Gal3-Mediated Downregulation of SOCS Expression by Synthetic Inhibitors A549 cells were grown in 12-well plates and incubated with 0~30 µg/ml of rhGal3 for 1 hour. After washing, RNA was extracted from the cells and subjected to reverse-transcription, followed by quantitative realtime PCR with designed primers for SOCS1, SOCS3, SOCS4, and beta-actin. Ct values were calculated and the relative expression level was calculated as $2^{(Ct\ actin-Ct\ target)}$. Data show the mean value of each sample in triplicate. Gal3 suppress SOCS expression in dose-dependent manner, with statistical significance in the 15 to 30 µg/ml range (FIGS. 16A-16C).

A549 cells were incubated with 0 or 30 µg of rhGal3 or that pre-mixed with TDG (50 mM) for one hour and analyzed as above. While disaccharide alone has some positive effect in SOCS expression, the mixture of galectin with disaccharide offset all the galectin's effect in suppressing SOCS expression, showing similar expression level as disaccharide alone (FIG. 17B: SOCS3, FIG. 17C: SOCS4) or slightly higher (FIG. 17A: SOCS1). A similar study yielded comparable results by preventing the downregulation of SOCS3 (FIG. 18).

Example 8—(a) Recovering Virulence Through Multiple Passing of the Sp3 Strain Through Mice, and (b) Standardized Lethal and Sub-Lethal Doses for the Virulent Sp3 Strain As described herein, synthesis of inhibitors of Gal3 binding was achieved for both monovalent and CD-based multivalent inhibitors, with non-reducing terminal galactosyl moieties, namely lactose (Lac), N-acetylgalactosamine (GalNAc), and the Thompsen-Friedenreich disaccharide (TFD; Galβ1,3GalNAc). The synthetic inhibitors not only prevented binding of Gal3 to desialylated glycoproteins such as asialofetuin, but also to airway epithelial cells (A549 cell line). Without wishing to be bound by any particular theory, the results show that the multivalent synthetic inhibitors are effective in hindering Gal3 binding. In addition, the effect of multivalency on enhanced affinity of the inhibitors for Gal3 was measured by SPR (Surface plasmon resonance) analysis, confirmed the semi-quantitative studies, and enabled to verify that for the multivalent inhibitors such as mvCD-TFD and mvCD-GalNAc, achieved affinities in the low M range (1-3 µM).

SPR analysis of monovalent vs multivalent inhibitors of Gal3 binding: the binding affinity/avidity of synthesized inhibitors of human Gal3 was determined by SPR analysis. Recombinant human Gal3 was immobilized onto CM5 chips in the presence of lactose (to protect its binding site during the binding process), the chip thoroughly washed with buffer, and the synthetic inhibitors were run through as analytes, at various concentrations. The $EC_{50}$ was determined as described at Bioorganic Med Chem 2013 21 2037-2044, using saturated RU values to plot a dose curve for each binding.

Results demonstrate that monovalent inhibitors have $EC_{50}$ higher than 1 mM, but their multivalent counterparts significantly increase their affinity/avidity to a µM scale: mvCD-TFD and mvCD-GalNAc have affinities below 4 (3.16 µM and 1.37 µM respectively), whereas the multivalent lactose (mvCD-Lac) has an affinity of 25.3 µM. Without wishing to be bound by any particular theory, this is consistent with the poor inhibitory activity of lactose for Gal3.

The result of IC$_{50}$ of multivalent and monovalent compounds on galectin-3 binding onto A549 cells was summarized in Table 1 for comparison purposes (right side column).

TABLE 1

Measurement of binding affinity and inhibition capacity of synthetic inhibitors for human Gal3

| Inhibitor | EC$_{50}$ (μM)* | IC$_{50}$ (μM)** |
|---|---|---|
| Lactose | 1469 | 95.2 |
| TDG | nd*** | 67.4 |
| mono Lac | >1,000 | 41.7 |
| mvCD-Lac | 25.3 | 22.3 |
| mono TFD | 1258 | >300 |
| mvCD-TFD | 3.16 | 10.4 |
| mono GalNAc | >1,000 | >300 |
| mvCD-GalNAc | 1.37 | 1.88 |

*SPR measurement to detect the affinity/avidity of carbohydrate ligands binding onto immobilized hGal3.
**Cell-based ELISA to detect the concentration of inhibitor to reach 50% inhibition of hGal3 binding onto fixed A549 cells.
***not determined The multivalent conjugation significantly decreased the IC$_{50}$ of the compounds from monovalents' larger than 300 μM to multivalents' 10 μM or less, with the exception of lactose. The IC$_{50}$ of monovalent lactose is 41.7 μM, much lower than other two monovalent inhibitors, just about two-fold of its multivalent counterpart. Similarly to the EC$_{50}$ values, mvCD-GalNAc has the lowest IC$_{50}$ of 1.88 μM, followed by mvCD-TFD with 10.4 μM, whereas mvCD-Lac has an IC$_{50}$ of 22.3 μM.

Determination of lethal and sub-lethal Sp3 dose: heterozygous littermates were intra-tracheally challenged with Sp3 from $10^4$ to $10^6$ (3 mice each group) and the survival and body weight of challenged mice were followed up for 6 days. Mice with the high Sp3 dose ($10^6$ bacteria) died within 2 to 3 days, and those that received $10^5$ got sick and started dying from day 2. Those animals that received $10^4$ showed slight body weight loss (FIG. 19A), and except for one animal that died at day 3, all others survived over 6 days (FIG. 19B). It was concluded that the virulence of the bacteria has been restored, and challenge dose with $10^4$ to $10^5$ is suitable for testing the protective effect of the synthetic inhibitors for Gal3.

REFERENCES

Alonso, J. M., A. Guiyoule, et al. (2003). "A model of meningococcal bacteremia after respiratory superinfection in influenza A virus-infected mice." FEMS Microbiol Lett 222(1): 99-106.
Arimori, Y., R. Nakamura, et al. (2013). "Type I interferon limits influenza virus-induced acute lung injury by regulation of excessive inflammation in mice." Antiviral Res 99(3): 230-237.
Bermejo-Martin, J. F., I. Martin-Loeches, et al. (2010). "Host adaptive immunity deficiency in severe pandemic influenza." Crit Care 14(5): R167.
Billiau, A. (2006). "Interferon: the pathways of discovery I. Molecular and cellular aspects." Cytokine Growth Factor Rev 17(5): 381-409.
Bode, J. G., S. Ludwig, et al. (2001). "The MKK6/p38 mitogen-activated protein kinase pathway is capable of inducing SOCS3 gene expression and inhibits IL-6-induced transcription." Biol Chem 382(10): 1447-1453.
Camby, I., M. Le Mercier, et al. (2006). "Galectin-1: a small protein with major functions." Glycobiology 16(16840800): 157.
Chertow, D. S. and M. J. Memoli (2013). "Bacterial coinfection in influenza: a grand rounds review." JAMA 309(3): 275-282.
Choi, Y. S., J. K. Park, et al. (2013). "Cytokine signaling-1 suppressor is inducible by IL-1beta and inhibits the catabolic effects of IL-1beta in chondrocytes: its implication in the paradoxical joint-protective role of IL-1beta." Arthritis Res Ther 15(6): R191.
Clark, A. R. and J. L. Dean (2012). "The p38 MAPK Pathway in Rheumatoid Arthritis: A Sideways Look." Open Rheumatol J 6: 209-219.
Croker, B. A., H. Kiu, et al. (2008). "SOCS regulation of the JAK/STAT signalling pathway." Semin Cell Dev Biol 19(4): 414-422.
Cross, A. S., S. W. Hyun, et al. (2012). "NEU1 and NEU3 sialidase activity expressed in human lung microvascular endothelia: NEU1 restrains endothelial cell migration, whereas NEU3 does not." J Biol Chem 287(19): 15966-15980.
Damjanovic, D., R. Lai, et al. (2013). "Marked improvement of severe lung immunopathology by influenza-associated pneumococcal superinfection requires the control of both bacterial replication and host immune responses." Am J Pathol 183(3): 868-880.
Davey, G. M., W. R. Heath, et al. (2006). "SOCS1: a potent and multifaceted regulator of cytokines and cell-mediated inflammation." Tissue Antigens 67(1): 1-9.
Ehlting, C., W. S. Lai, et al. (2007). "Regulation of suppressor of cytokine signaling 3 (SOCS3) mRNA stability by TNF-alpha involves activation of the MKK6/p38MAPK/MK2 cascade." J Immunol 178(5): 2813-2826.
Farnworth, S. L., N. C. Henderson, et al. (2008). "Galectin-3 reduces the severity of pneumococcal pneumonia by augmenting neutrophil function." Am J Pathol 172(2): 395-405.
Feng, C., A. Ghosh, et al. (2013). "The galectin CvGal1 from the eastern oyster (Crassostrea *virginica*) binds to blood group A oligosaccharides on the hemocyte surface." J Biol Chem 288(34): 24394-24409.
Feng, C., N. M. Stamatos, et al. (2012). "Sialyl residues modulate LPS-mediated signaling through the Toll-like receptor 4 complex." PLoS One 7(4): e32359.
Feng, C., L. Zhang, et al. (2013). "Neuraminidase reprograms lung tissue and potentiates lipopolysaccharide-induced acute lung injury in mice." J Immunol 191(9): 4828-4837.
Fischer, C., H. Sanchez-Ruderisch, et al. (2005). "Galectin-1 interacts with the {alpha}5 {beta} 1 fibronectin receptor to restrict carcinoma cell growth via induction of p21 and p27." J Biol Chem 280(44): 37266-37277.
Fletcher, J. and R. Starr (2005). "The role of suppressors of cytokine signalling in thymopoiesis and T cell activation." Int J Biochem Cell Biol 37(9): 1774-1786.
Fukuyama, S. and Y. Kawaoka (2011). "The pathogenesis of influenza virus infections: the contributions of virus and host factors." Curr Opin Immunol 23(4): 481-486.
Gianni, T. and G. Campadelli-Fiume (2014). "The epithelial alphavbeta3-integrin boosts the MYD88-dependent TLR2 signaling in response to viral and bacterial components." PLoS Pathog 10(11): e1004477.
Gianni, T., V. Leoni, et al. (2012). "alphavbeta3-integrin is a major sensor and activator of innate immunity to herpes simplex virus-1." Proc Natl Acad Sci USA 109(48): 19792-19797.

Gonzalez-Navajas, J. M., J. Lee, et al. (2012). "Immunomodulatory functions of type I interferons." Nat Rev Immunol 12(2): 125-135.

Guarda, G., M. Braun, et al. (2011). "Type I interferon inhibits interleukin-1 production and inflammasome activation." Immunity 34(2): 213-223.

Ilangumaran, S., S. Ramanathan, et al. (2004). "Regulation of the immune system by SOCS family adaptor proteins." Semin Immunol 16(6): 351-365.

Kedzierski, L., E. M. Linossi, et al. (2014). "Suppressor of cytokine signaling 4 (SOCS4) protects against severe cytokine storm and enhances viral clearance during influenza infection." PLoS Pathog 10(5): e1004134.

Kiu, H., D. J. Hilton, et al. (2007). "Mechanism of crosstalk inhibition of IL-6 signaling in response to LPS and TNFalpha." Growth Factors 25(5): 319-328.

Koh, H. S., C. Lee, et al. (2008). "CD7 expression and galectin-1-induced apoptosis of immature thymocytes are directly regulated by NF-kappaB upon T-cell activation." Biochem Biophys Res Commun 370(1): 149-153.

Lillehoj, E. P., S. W. Hyun, et al. (2012). "NEU1 sialidase expressed in human airway epithelia regulates epidermal growth factor receptor (EGFR) and MUC1 protein signaling." J Biol Chem 287(11): 8214-8231.

Luo, M. (2012). "Influenza virus entry." Adv Exp Med Biol 726: 201-221.

Matsumiya, T. and D. M. Stafforini (2010). "Function and regulation of retinoic acid-inducible gene-I." Crit Rev Immunol 30(6): 489-513.

Monsalvo, A. C., J. P. Batalle, et al. (2011). "Severe pandemic 2009 H1N1 influenza disease due to pathogenic immune complexes." Nat Med 17(2): 195-199.

Naka, T., M. Fujimoto, et al. (2005). "Negative regulation of cytokine and TLR signalings by SOCS and others." Adv Immunol 87: 61-122.

Nguyen, K. B., T. P. Salazar-Mather, et al. (2002). "Coordinated and distinct roles for IFN-alpha beta, IL-12, and IL-15 regulation of NK cell responses to viral infection." J Immunol 169(8): 4279-4287.

Nita-Lazar, M., A. Banerjee, et al. (2015a). "Desialylation of airway epithelial cells during influenza virus infection enhances pneumococcal adhesion via galectin binding." Mol Immunol 65(1): 1-16.

Nita-Lazar M, et al. (2015b). "Galectins regulate the inflammatory response in airway epithelial cells exposed to microbial neuraminidase by modulating the expression of SOCS1 and RIG1". Mol Immunol. 68(2 Pt A): 194-202.

Pauli, E. K., M. Schmolke, et al. (2008). "Influenza A virus inhibits type I IFN signaling via NF-kappaB-dependent induction of SOCS-3 expression." PLoS Pathog 4(11): e1000196.

Perera, P. Y., T. N. Mayadas, et al. (2001). "CD11b/CD18 acts in concert with CD14 and Toll-like receptor (TLR) 4 to elicit full lipopolysaccharide and taxol-inducible gene expression." J Immunol 166(1): 574-581.

Poltorak, A., X. He, et al. (1998). "Defective LPS signaling in C3H/HeJ and $C_{57}$BL/10ScCr mice: mutations in Tlr4 gene." Science 282(5396): 2085-2088.

Pothlichet, J., M. Chignard, et al. (2008). "Cutting edge: innate immune response triggered by influenza A virus is negatively regulated by SOCS1 and SOCS3 through a RIG-I/IFNAR1-dependent pathway." J Immunol 180(4): 2034-2038.

Rabinovich, G. A., G. Daly, et al. (1999). "Recombinant galectin-1 and its genetic delivery suppress collagen-induced arthritis via T cell apoptosis." J Exp Med 190(3): 385-398.

Rabinovich, G. A. and J. M. Ilarregui (2009). "Conveying glycan information into T-cell homeostatic programs: a challenging role for galectin-1 in inflammatory and tumor microenvironments." Immunol Rev 230(1): 144-159.

Ramirez-Martinez, G., A. Cruz-Lagunas, et al. (2013). "Seasonal and pandemic influenza H1N1 viruses induce differential expression of SOCS-1 and RIG-I genes and cytokine/chemokine production in macrophages." Cytokine 62(1): 151-159.

Santucci, L., S. Fiorucci, et al. (2003). "Galectin-1 suppresses experimental colitis in mice." Gastroenterology 124(5): 1381-1394.

Sato, S., N. Ouellet, et al. (2002). "Role of galectin-3 as an adhesion molecule for neutrophil extravasation during streptococcal pneumonia." J Immunol 168(4): 1813-1822.

Seki, M., Y. Higashiyama, et al. (2004). "Acute infection with influenza virus enhances susceptibility to fatal pneumonia following *Streptococcus pneumoniae* infection in mice with chronic pulmonary colonization with *Pseudomonas aeruginosa*." Clin Exp Immunol 137(1): 35-40.

Speshock, J. L., N. Doyon-Reale, et al. (2007). "Filamentous influenza A virus infection predisposes mice to fatal septicemia following superinfection with *Streptococcus pneumoniae* serotype 3." Infect Immun 75(6): 3102-3111.

Takeuchi, O. and S. Akira (2008). "MDA5/RIG-I and virus recognition." Curr Opin Immunol 20(1): 17-22.

Toscano, M. A., L. Campagna, et al. (2011). "Nuclear factor (NF)-kappaB controls expression of the immunoregulatory glycan-binding protein galectin-1." Mol Immunol 48(15-16): 1940-1949.

Toscano, M. A., A. G. Commodaro, et al. (2006). "Galectin-1 suppresses autoimmune retinal disease by promoting concomitant Th2- and T regulatory-mediated anti-inflammatory responses." J Immunol 176(10): 6323-6332.

Vasta, G. R. (2009). "Roles of galectins in infection." Nat Rev Microbiol 7(6): 424-438.

Vasta, G. R. and H. Ahmed (2008). Animal Lectins: A Functional View, CRC Press.

Xu, X., J. Zheng, et al. (2014). "Respiratory syncytial virus NS1 protein degrades STAT2 by inducing SOCS1 expression." Intervirology 57(2): 65-73.

Yang, X. X., N. Du, et al. (2010). "Gene expression profiles comparison between 2009 pandemic and seasonal H1N1 influenza viruses in A549 cells." Biomed Environ Sci 23(4): 259-266.

Yee, N. K. and J. A. Hamerman (2013). "beta(2) integrins inhibit TLR responses by regulating NF-kappaB pathway and p38 MAPK activation." Eur J Immunol 43(3): 779-792.

Yoneyama, M. and T. Fujita (2009). "RNA recognition and signal transduction by RIG-I-like receptors." Immunol Rev 227(1): 54-65.

Yoo, J. S., H. Kato, et al. (2014). "Sensing viral invasion by RIG-I like receptors." Curr Opin Microbiol 20: 131-138.

Yoshimura, A., T. Naka, et al. (2007). "SOCS proteins, cytokine signalling and immune regulation." Nat Rev Immunol 7(6): 454-465.

Zimmermann, S., P. J. Murray, et al. (2006). "Induction of suppressor of cytokine signaling-1 by *Toxoplasma gondii* contributes to immune evasion in macrophages by blocking IFN-gamma signaling." J Immunol 176(3): 1840-1847.

Zuniga, J., M. Torres, et al. (2011). "Inflammatory profiles in severe pneumonia associated with the pandemic influenza A/H1N1 virus isolated in Mexico City." Autoimmunity 44(7): 562-570.

It is claimed:

1. A galectin 3 inhibitor of formula I, II, or III:

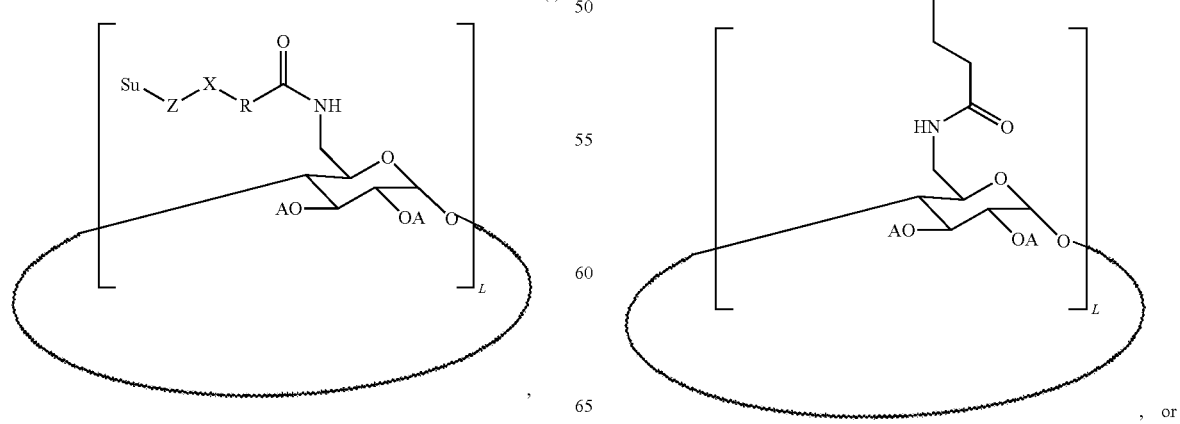

-continued (III)

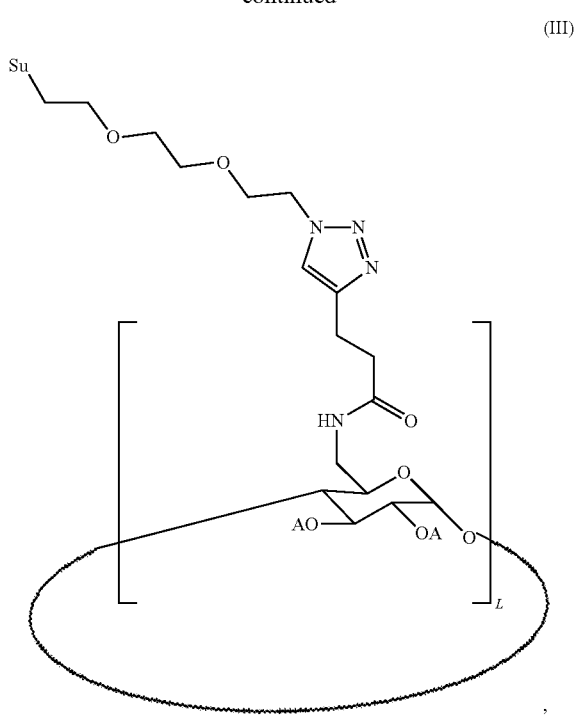

wherein Su is a monosaccharide or disaccharide moiety;

L is an integer of 6, 7, or 8;

R is a bond or a substituent selected from the group consisting of —(CH$_2$)$_n$—, —(CH$_2$CH$_2$O)$_n$—, —(CH$_2$CH$_2$CH$_2$O)$_n$—, optionally substituted -(alkyl)$_n$-, and optionally substituted -(alkoxy)$_n$-, wherein n is an integer of 1 to 20;

A is H or —C(O)—(CH$_2$)$_k$—CH$_3$, wherein k is an integer of 3 to 7;

X is a bond or a triazolyl;

Z is a bond or a substituent selected from the group consisting of substituted or unsubstituted alkyl, heteroalkyl, alkoxy, -alkoxyalkyl-, -alkylalkoxy)$_m$-, and -(alkoxy)$_m$-alkyl-, wherein m is independently an integer of 1 to 20; and a pharmaceutically acceptable salt thereof.

2. The galectin 3 inhibitor of claim 1, wherein the monosaccharide moiety is

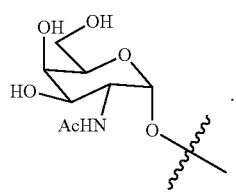 [SMILES: *OC1OC(CO)C(O)C(O)C1NC(C)=O]

3. The galectin 3 inhibitor of claim 1, wherein the disaccharide moiety is

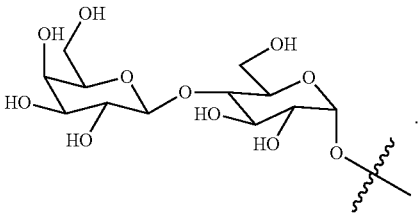 [SMILES: *OC1OC(CO)C(OC2OC(CO)C(O)C(O)C2O)C(O)C1O]

4. The galectin 3 inhibitor of claim 1, wherein the disaccharide moiety is

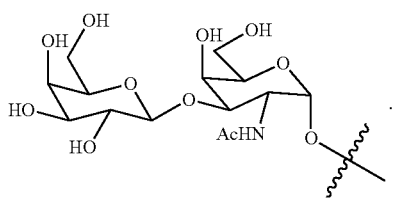 [SMILES: *OC1OC(CO)C(O)C(OC2OC(CO)C(O)C(O)C2O)C1NC(C)=O]

5. The galectin 3 inhibitor of claim 1, wherein L is 7.

6. The galectin 3 inhibitor of claim 1, wherein A is —C(O)—(CH$_2$)$_k$—CH$_3$, and k is an integer of 4 to 6.

7. The galectin 3 inhibitor of claim 6, wherein k is 4.

8. The galectin 3 inhibitor of claim 1, wherein A is H.

9. The galectin 3 inhibitor of claim 1, wherein R is —(CH$_2$)$_m$—, and m is an integer of 1 to 3.

10. The galectin 3 inhibitor of claim 1, wherein R is —(CH$_2$)$_2$—.

11. The galectin 3 inhibitor of claim 1, wherein X is

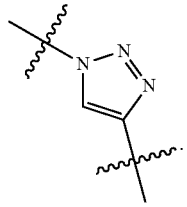

12. The galectin 3 inhibitor of claim 1, wherein Z is -alkyl-(CH$_2$O)$_{k'}$—, -alkyl-(CH$_2$CH$_2$O)$_{k'}$—, -alkyl-(CH$_2$CH$_2$CH$_2$O)$_{k'}$—, —(CH$_2$O)$_{k'}$-alkyl-, —(CH$_2$CH$_2$O)$_{k'}$-alkyl-, or —(CH$_2$CH$_2$CH$_2$O)$_{k'}$-alkyl-, and k' is an integer of 1 to 5.

13. A pharmaceutical formulation for treating septic shock by inhibiting galectin 3 activity in a patient in need thereof, the pharmaceutical formulation comprising a therapeutically effective amount of a galectin 3 inhibitor of claim 1, or a pharmaceutically acceptable salt thereof, and a pharmaceutically acceptable carrier.

14. A method of treating septic shock by inhibiting galectin 3 activity in a patient in need thereof, the method comprising administering a therapeutically effective amount of a galectin 3 inhibitor of claim 1, or a pharmaceutically acceptable salt thereof.

15. The method of claim 14, wherein the patient has pneumococcal pneumonia.

16. The method of claim 14, wherein administering the therapeutically effective amount of the galectin 3 inhibitor comprises oral or intranasal administration.

17. The method of claim 14, wherein the method further comprises administering a therapeutically effective amount of an additional active agent selected from the group consisting of cefazolin, nafcillin, vancomycin, cefoxitin, neomycin plus erythromycin, penicillin G, trimethoprim plus sulfamethoxazole, and clindamycin or clindamycin plus gentamycin or tobramycin.

18. The pharmaceutical formulation of claim 13, wherein the galectin 3 inhibitor is included in a micelle.

19. The method of claim 14, wherein the galectin 3 inhibitor is included in a micelle.

20. A method of treating sepsis by inhibiting galectin 3 activity in a patient in need thereof, the method comprising administering a therapeutically effective amount of a galectin 3 inhibitor of claim 1, or a pharmaceutically acceptable salt thereof.

21. The method of claim 20, wherein the patient has pneumococcal pneumonia.

22. The method of claim 20, wherein administering the therapeutically effective amount of the galectin 3 inhibitor comprises oral or intranasal administration.

23. The method of claim 20, wherein the method further comprises administering a therapeutically effective amount of an additional active agent selected from the group consisting of cefazolin, nafcillin, vancomycin, cefoxitin, neomycin plus erythromycin, penicillin G, trimethoprim plus sulfamethoxazole, and clindamycin or clindamycin plus gentamycin or tobramycin.

24. The method of claim 20, wherein the galectin 3 inhibitor is included in a micelle.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: human SOCS1 forward primer

<400> SEQUENCE: 1
ttttcgccct tagcgtgaa                                                19

<210> SEQ ID NO 2
<211> LENGTH: 19
<212> TYPE: DNA
<213> ORGANISM: Artificial Sequence
<220> FEATURE:
<223> OTHER INFORMATION: human SOCS1 reverse primer

<400> SEQUENCE: 2
gcggcgcggc gccgccacg                                                19

<210> SEQ ID NO 3
<211> LENGTH: 18
<212> TYPE: DNA
<213> ORGANISM: Artificial Sequence
<220> FEATURE:
<223> OTHER INFORMATION: human RIG1 forward primer

<400> SEQUENCE: 3
accagacctc ctcttggc                                                 18

<210> SEQ ID NO 4
<211> LENGTH: 18
<212> TYPE: DNA
<213> ORGANISM: Artificial Sequence
<220> FEATURE:
<223> OTHER INFORMATION: human RIG1 reverse primer

<400> SEQUENCE: 4 gaagggcag atggctgt                                                  18

<210> SEQ ID NO 5
<211> LENGTH: 20
<212> TYPE: DNA
<213> ORGANISM: Artificial Sequence
<220> FEATURE:
<223> OTHER INFORMATION: human beta-actin forward primer

<400> SEQUENCE: 5
ccgcgctcgt cgtcgacaac                                               20

<210> SEQ ID NO 6
<211> LENGTH: 19
<212> TYPE: DNA
<213> ORGANISM: Artificial Sequence
<220> FEATURE:
<223> OTHER INFORMATION: human beta-actin reverse primer

<400> SEQUENCE: 6
gctctgggcc tcgtcgccc                                                19
```

```
<210> SEQ ID NO 7
<211> LENGTH: 20
<212> TYPE: DNA
<213> ORGANISM: Artificial Sequence
<220> FEATURE:
<223> OTHER INFORMATION: human SOCS1 forward primer

<400> SEQUENCE: 7
gacgcctgcg gattctactg                                          20

<210> SEQ ID NO 8
<211> LENGTH: 20
<212> TYPE: DNA
<213> ORGANISM: Artificial Sequence
<220> FEATURE:
<223> OTHER INFORMATION: human SOCS1 reverse primer

<400> SEQUENCE: 8
cacgctaagg gcgaaaaagc                                          20

<210> SEQ ID NO 9
<211> LENGTH: 22
<212> TYPE: DNA
<213> ORGANISM: Artificial Sequence
<220> FEATURE:
<223> OTHER INFORMATION: human RPS13 primer

<400> SEQUENCE: 9
cgaaagcatc ttgagaggaa ca                                       22

<210> SEQ ID NO 10
<211> LENGTH: 19
<212> TYPE: DNA
<213> ORGANISM: Artificial Sequence
<220> FEATURE:
<223> OTHER INFORMATION: human RPS13 reverse primer

<400> SEQUENCE: 10
tcgagccaaa cggtgaatc                                           19
```